(12) United States Patent
Prodoehl et al.

(10) Patent No.: US 8,927,092 B2
(45) Date of Patent: *Jan. 6, 2015

(54) WEB SUBSTRATES HAVING WIDE COLOR GAMUT INDICIA PRINTED THEREON

(75) Inventors: Michael Scott Prodoehl, West Chester, OH (US); Kevin Benson McNeil, Loveland, OH (US); Thomas Timothy Byrne, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 69 days.

This patent is subject to a terminal disclaimer.

(21) Appl. No.: 13/040,345

(22) Filed: Mar. 4, 2011

(65) Prior Publication Data

US 2012/0225262 A1 Sep. 6, 2012

(51) Int. Cl.
- *B32B 3/10* (2006.01)
- *D21H 19/66* (2006.01)
- *D21H 27/00* (2006.01)

(52) U.S. Cl.
CPC ............ *D21H 19/66* (2013.01); *D21H 27/002* (2013.01)
USPC ..................................................... 428/195.1

(58) Field of Classification Search
CPC ............................. D21H 19/66; D21H 27/002
See application file for complete search history.

(56) References Cited

U.S. PATENT DOCUMENTS

| | | |
|---|---|---|
| 1,867,314 A | 7/1932 | Gurwick |
| 2,226,163 A | 12/1940 | DuFour |
| 2,427,765 A | 9/1947 | Chollar |
| 2,468,400 A | 4/1949 | Huebner |
| 2,864,310 A | 12/1958 | Nelson |
| 3,055,296 A | 9/1962 | Farrow |
| 3,056,384 A | 10/1962 | Beale |
| 3,294,016 A | 12/1966 | Heonis |
| 3,301,746 A | 1/1967 | Sanford et al. |
| 3,473,576 A | 10/1969 | Amneus |
| 3,573,164 A | 3/1971 | Friedberg et al. |
| 3,738,269 A | 6/1973 | Wagner |
| 3,821,068 A | 6/1974 | Shaw |
| 3,896,722 A | 7/1975 | Farrow |
| 3,896,723 A | 7/1975 | Farrow et al. |
| 3,974,025 A | 8/1976 | Ayers |
| 3,994,771 A | 11/1976 | Morgan, Jr. et al. |
| 4,033,258 A | 7/1977 | Farrow |
| 4,191,609 A | 3/1980 | Trokhan |
| 4,191,756 A | 3/1980 | Masi et al. |
| 4,239,065 A | 12/1980 | Trokhan |
| 4,300,981 A | 11/1981 | Carstens |
| 4,361,089 A | 11/1982 | Wittkopf et al. |
| 4,437,408 A | 3/1984 | Arkans |

(Continued)

FOREIGN PATENT DOCUMENTS

| | | |
|---|---|---|
| EP | 1 075 948 B1 | 9/2005 |
| EP | 1 673 225 B1 | 8/2008 |

(Continued)

*Primary Examiner* — Bruce H Hess
*Assistant Examiner* — Sathavaram I Reddy
(74) *Attorney, Agent, or Firm* — Peter D. Meyer

(57) ABSTRACT

A web substrate having indicia having X colors disposed thereon is disclosed. The indicia are disposed upon the web substrate by a contact printing system adapted to print the X colors upon the web substrate utilizing X-Y printing components. X and Y are whole numbers, $0<Y<X$, and $X>1$. Each of the X colors is defined by $L^*a^*b^*$ color values defined by CIELab coordinate values disposed inside the boundary described by a system of equations.

18 Claims, 8 Drawing Sheets

(56) References Cited

U.S. PATENT DOCUMENTS

| | | | |
|---|---|---|---|
| 4,440,597 A | 4/1984 | Wells et al. |
| 4,452,141 A | 6/1984 | Mistyurik |
| 4,458,399 A | 7/1984 | Kessler |
| 4,483,053 A | 11/1984 | Hamisch, Jr. |
| 4,528,239 A | 7/1985 | Trokhan |
| 4,529,480 A | 7/1985 | Trokhan |
| 4,534,094 A | 8/1985 | Kessler |
| 4,574,732 A | 3/1986 | Verwey et al. |
| 4,599,627 A | 7/1986 | Vollert |
| 4,637,859 A | 1/1987 | Trokhan |
| 4,766,840 A | 8/1988 | Beckley et al. |
| 4,812,899 A | 3/1989 | Kueppers |
| 4,844,952 A | 7/1989 | Korenkiewicz et al. |
| 4,878,977 A | 11/1989 | Kueppers |
| 4,939,992 A | 7/1990 | Bird |
| 5,082,703 A | 1/1992 | Longobardi |
| 5,282,419 A | 2/1994 | Barrois |
| 5,364,504 A | 11/1994 | Smurkoski et al. |
| 5,429,686 A | 7/1995 | Chiu et al. |
| 5,458,590 A | 10/1995 | Schleinz et al. |
| 5,529,664 A | 6/1996 | Trokhan et al. |
| 5,549,790 A | 8/1996 | Van Phan |
| 5,556,509 A | 9/1996 | Trokhan et al. |
| 5,580,423 A | 12/1996 | Ampulski et al. |
| 5,609,725 A | 3/1997 | Van Phan |
| 5,629,052 A | 5/1997 | Trokhan et al. |
| 5,637,194 A | 6/1997 | Ampulski et al. |
| 5,672,248 A | 9/1997 | Wendt et al. |
| 5,674,663 A | 10/1997 | McFarland et al. |
| 5,679,222 A | 10/1997 | Rasch et al. |
| 5,693,187 A | 12/1997 | Ampulski et al. |
| 5,695,855 A | 12/1997 | Yeo et al. |
| 5,709,775 A | 1/1998 | Trokhan et al. |
| 5,714,041 A | 2/1998 | Ayers et al. |
| 5,733,634 A | 3/1998 | Karel |
| 5,734,800 A | 3/1998 | Herbert et al. |
| 5,776,307 A | 7/1998 | Ampulski et al. |
| 5,795,440 A | 8/1998 | Ampulski et al. |
| 5,814,190 A | 9/1998 | Van Phan |
| 5,817,377 A | 10/1998 | Trokhan et al. |
| 5,846,379 A | 12/1998 | Ampulski et al. |
| 5,855,739 A | 1/1999 | Ampulski et al. |
| 5,858,514 A | 1/1999 | Bowers |
| 5,861,082 A | 1/1999 | Ampulski et al. |
| 5,865,950 A | 2/1999 | Vinson et al. |
| 5,871,887 A | 2/1999 | Trokhan et al. |
| 5,897,745 A | 4/1999 | Ampulski et al. |
| 5,904,811 A | 5/1999 | Ampulski et al. |
| 5,906,161 A | 5/1999 | Kessler |
| 5,906,710 A | 5/1999 | Trokhan |
| 5,942,085 A | 8/1999 | Neal et al. |
| 6,048,938 A | 4/2000 | Neal et al. |
| 6,096,412 A | 8/2000 | McFarland et al. |
| 6,173,646 B1 | 1/2001 | Tanaka et al. |
| 6,187,138 B1 | 2/2001 | Neal et al. |
| 6,234,078 B1 | 5/2001 | Kessler |
| 6,281,269 B1 | 8/2001 | Schut |
| 6,477,948 B1 | 11/2002 | Nissing et al. |
| 6,610,131 B2 | 8/2003 | Harris et al. |
| 6,993,964 B2 | 2/2006 | Franz et al. |
| 7,611,582 B2 | 11/2009 | McNeil et al. |
| 8,163,132 B2 | 4/2012 | Kien |
| 2006/0008514 A1 | 1/2006 | Koenig et al. |

FOREIGN PATENT DOCUMENTS

| | | |
|---|---|---|
| GB | 1176321 | 1/1970 |
| GB | 1241793 | 8/1971 |
| GB | 1241794 | 8/1971 |
| GB | 1350059 | 4/1974 |
| GB | 1396282 | 6/1975 |
| GB | 1439458 | 6/1976 |
| GB | 1468360 | 3/1977 |
| GB | 1570545 | 7/1980 |
| GB | 2314292 | 12/1997 |
| WO | WO 84/00516 | 2/1984 |
| WO | WO 99/54143 | 10/1999 |

WEB SUBSTRATES HAVING WIDE COLOR GAMUT INDICIA PRINTED THEREON

FIELD OF THE INVENTION

This disclosure relates, in general, to web substrates such as tissue paper products. More specifically, this disclosure relates to tissue paper products having indicia having a unique color gamut applied thereto.

BACKGROUND OF THE INVENTION

Absorbent paper products are a staple of everyday life. Absorbent paper products are used as consumer products for paper towels, toilet tissue, facial tissue, napkins, and the like. The large demand for such paper products has created a demand for improved aesthetics, visual effects, and other benefits on the surface of the product, and as a result, improved methods of creating these visual effects.

Many consumers prefer absorbent paper products that have a design, or other artwork, printed thereon. For example, during specific holidays, consumers sometimes choose a paper towel product that compliments that holiday.

In the art of absorbent paper products, printed indicia may be provided onto the substrate surfaces using process printing processes which often offer an overall positive consumer response. However, typical prior art process printing methodology and apparatus for absorbent paper products is often limited to having four colors as the basis for generating the resulting color palette. The prior art process printing allows producers and manufacturers with the benefit of absorbent paper products with the ability to print on absorbent paper product substrates at a speed that is commercially viable. Those of skill in the art will appreciate that the substrates used for many absorbent paper products, especially through air dried and other formed substrates, have properties such as a relatively low modulus, a highly textured surface, and other physical properties that make such a substrate difficult to print on using conventional high-speed printing processes/apparatus. While practical, the prior art processes for printing on absorbent paper product substrates are held to a four color base for printing, and, as a result, are unable to capture as wide of a color palette as a process/apparatus that takes advantage of a larger number of base colors. Without wishing to be limited by theory, it is thought that providing an absorbent paper product with a color palette that exceeds the prior art color palette (i.e., a product having more vibrant, intricate, or bright printed pattern thereon) will delight the consumer.

Kien, US 2009-0114354 A1, discloses color gamut boundaries defined by the following system of 2-dimensional equations in CIELab coordinates (2-D gamut), respectively:

$$\{a^*=-41.2 \text{ to } -29.0; b^*=3.6 \text{ to } 52.4\} \rightarrow b^*=4 a^*+168.4$$

$$\{a^*=-29 \text{ to } -6.4; b^*=52.4 \text{ to } 64.9\} \rightarrow b^*=0.553097 a^*+68.4398$$

$$\{a^*=-6.4 \text{ to } 33.4; b^*=64.9 \text{ to } 42.8\} \rightarrow b^*=-0.553097 a^*+61.3462$$

$$\{a^*=33.4 \text{ to } 58.0; b^*=42.8 \text{ to } 12.5\} \rightarrow b^*=-1.23171 a^*+83.939$$

$$\{a^*=58.0 \text{ to } 25.8; b^*=12.5 \text{ to } -28.2\} \rightarrow b^*=1.26398 a^*-60.8106$$

$$\{a^*=25.8 \text{ to } -9.6; b^*=-28.2 \text{ to } -43.4\} \rightarrow b^*=0.429379 a^*-39.278$$

$$\{a^*=-9.6 \text{ to } -41.2; b^*=-43.4 \text{ to } 3.6\} \rightarrow b^*=-1.48734 a^*-57.6785$$

where $L^*$ ranges from 0 to 100.

More specifically, Kien provides the extrapolated color gamut boundaries defined by the following system of 3-dimensional equations in CIELab coordinates (3-D gamut), respectively:

| Vertexes defining each Face ||||||||| $E a^* + F b^* + G L^* + H = 0$ ||||
|---|---|---|---|---|---|---|---|---|---|---|---|---|
| Vertex 1 ||| Vertex 2 ||| Vertex 3 ||| | | | |
| z1 | x1 | y1 | z2 | x2 | y2 | z3 | x3 | y3 | Face Plane Equation Coefficients ||||
| $L^*$ | $a^*$ | $b^*$ | $L^*$ | $a^*$ | $b^*$ | $L^*$ | $a^*$ | $b^*$ | E | F | G | H |
| 67.7 | −33.5 | 46.7 | 66.7 | 33.4 | 42.8 | 87.6 | −6.1 | 66.5 | −57.8 | −1358.7 | 1431.5 | −35396.1 |
| 67.7 | −33.5 | 46.7 | 87.6 | −6.1 | 66.5 | 93.1 | −5.6 | 48.8 | 461.1 | −140.8 | −494.9 | 55524.3 |
| 67.7 | −33.5 | 46.7 | 66.7 | 33.4 | 42.8 | 36 | −2.2 | 4.6 | 81.5 | 2089.4 | −2694.4 | 87567.1 |
| 67.7 | −33.5 | 46.7 | 36 | −2.2 | 4.6 | 56.4 | −41.2 | 3.6 | −890.5 | 597.8 | −1673.2 | 55526.2 |
| 67.7 | −33.5 | 46.7 | 79.3 | −15.9 | −15.8 | 56.4 | −41.2 | 3.6 | 1206.2 | 109.6 | −1239.8 | 119226.7 |
| 67.7 | −33.5 | 46.7 | 93.1 | −5.6 | 48.8 | 79.3 | −15.9 | −15.8 | 1611.9 | 123.4 | −1780.7 | 168788.6 |
| 66.7 | 33.4 | 42.8 | 87.6 | −6.1 | 66.5 | 93.1 | −5.6 | 48.8 | 500.3 | 227.7 | 687.3 | −72297.8 |
| 66.7 | 33.4 | 42.8 | 93.1 | −5.6 | 48.8 | 94.3 | −0.3 | 2 | 1242.7 | 186.7 | 1793.4 | −169118.2 |
| 66.7 | 33.4 | 42.8 | 94.3 | −0.3 | 2 | 80.6 | 16.9 | −5.9 | 777.0 | 13.0 | 968.0 | −91074.4 |
| 66.7 | 33.4 | 42.8 | 80.6 | 16.9 | −5.9 | 65.2 | 42.4 | −5.7 | 747.2 | 100.4 | 1238.6 | −111862.7 |
| 66.7 | 33.4 | 42.8 | 65.2 | 42.4 | −5.7 | 52.1 | 58 | 12.5 | 662.7 | 94.5 | 920.4 | −87567.8 |
| 66.7 | 33.4 | 42.8 | 52.1 | 58 | 12.5 | 36 | −2.2 | 4.6 | 372.5 | 1275.0 | −2018.4 | 67617.0 |
| 93.1 | −5.6 | 48.8 | 94.3 | −0.3 | 2 | 79.3 | −15.9 | −15.8 | 723.4 | 60.8 | −824.4 | 77838.3 |
| 94.3 | −0.3 | 2 | 79.3 | −15.9 | −15.8 | 80.6 | 16.9 | −5.9 | 125.4 | −471.7 | 429.4 | −39511.4 |
| 79.3 | −15.9 | −15.8 | 80.6 | 16.9 | −5.9 | 59.3 | −20.7 | −36.4 | −171.2 | 649.8 | −628.2 | 57356.9 |
| 79.3 | −15.9 | −15.8 | 56.4 | −41.2 | 3.6 | 59.3 | −20.7 | −36.4 | −859.7 | −396.1 | 614.3 | −68641.9 |
| 80.6 | 16.9 | −5.9 | 65.2 | 42.4 | −5.7 | 61.3 | 18.4 | −27.6 | −338.0 | 469.1 | −553.7 | 53104.5 |
| 80.6 | 16.9 | −5.9 | 59.3 | −20.7 | −36.4 | 61.3 | 18.4 | −27.6 | 126.4 | −757.6 | 861.7 | −76057.5 |
| 65.2 | 42.4 | −5.7 | 52.1 | 58 | 12.5 | 42.5 | 25.8 | −28.2 | −707.9 | 571.6 | −48.9 | 36459.5 |
| 65.2 | 42.4 | −5.7 | 42.5 | 25.8 | −28.2 | 61.3 | 18.4 | −27.6 | −409.4 | 480.1 | −176.5 | 31599.2 |
| 52.1 | 58 | 12.5 | 36 | −2.2 | 4.6 | 42.5 | 25.8 | −28.2 | −579.4 | −59.5 | 2195.8 | −80048.4 |
| 36 | −2.2 | 4.6 | 56.4 | −41.2 | 3.6 | 48 | −9.6 | −43.4 | 967.2 | 317.0 | 1864.6 | −66456.1 |
| 36 | −2.2 | 4.6 | 48 | −9.6 | −43.4 | 42.5 | 25.8 | −28.2 | 81.6 | 384.1 | 1586.7 | −58709.3 |

-continued

| Vertexes defining each Face | | | | | | | | | E a* + F b* + G L* + H = 0 | | | |
|---|---|---|---|---|---|---|---|---|---|---|---|---|
| Vertex 1 | | | Vertex 2 | | | Vertex 3 | | | Face Plane Equation Coefficients | | | |
| z1 | x1 | y1 | z2 | x2 | y2 | z3 | x3 | y3 | E | F | G | H |
| L* | a* | b* | L* | a* | b* | L* | a* | b* | | | | |
| 56.4 | −41.2 | 3.6 | 59.3 | −20.7 | −36.4 | 48 | −9.6 | −43.4 | 472.3 | 263.8 | 300.5 | 1560.7 |
| 59.3 | −20.7 | −36.4 | 48 | −9.6 | −43.4 | 61.3 | 18.4 | −27.6 | 85.4 | −464.0 | 371.4 | −37144.9 |
| 48 | −9.6 | −43.4 | 42.5 | 25.8 | −28.2 | 61.3 | 18.4 | −27.6 | 289.1 | −624.8 | 133.7 | −30760.8 |

Accordingly, it is desired to provide a printing process and apparatus for providing an absorbent paper product that has a relatively wide color palette.

SUMMARY OF THE INVENTION

The web substrate of the present disclosure has indicia having X colors disposed thereon. The indicia are disposed upon the web substrate by a contact printing system adapted to print the X colors upon the web substrate utilizing X-Y printing components. X and Y are whole numbers, 0<Y<X, and X>1. Each of the X colors is defined by L*a*b* color values defined by CIELab coordinate values disposed inside the boundary described by the following system of equations:

$$\{a^*=-54.1 \text{ to } 72.7; b^*=131.5 \text{ to } 145.8\} \rightarrow b^*=0.113 a^*+137.6$$

$$\{a^*=-131.6 \text{ to } -54.1; b^*=89.1 \text{ to } 131.5\} \rightarrow b^*=0.547 a^*+161.1$$

$$\{a^*=-165.6 \text{ to } -131.6; b^*=28.0 \text{ to } 89.1\} \rightarrow b^*=1.797 a^*+325.6$$

$$\{a^*=3.6 \text{ to } -165.6; b^*=-82.6 \text{ to } 28.0\} \rightarrow b^*=-0.654 a^*-80.3$$

$$\{a^*=127.1 \text{ to } 3.6; b^*=-95.1 \text{ to } -82.6\} \rightarrow b^*=-0.101 a^*-82.3$$

$$\{a^*=72.7 \text{ to } 127.1; b^*=145.8 \text{ to } -95.1\} \rightarrow b^*=-4.428 a^*+467.7$$

where L* ranges from 0 to 100.

DETAILED DESCRIPTION OF THE INVENTION

Figure 1:
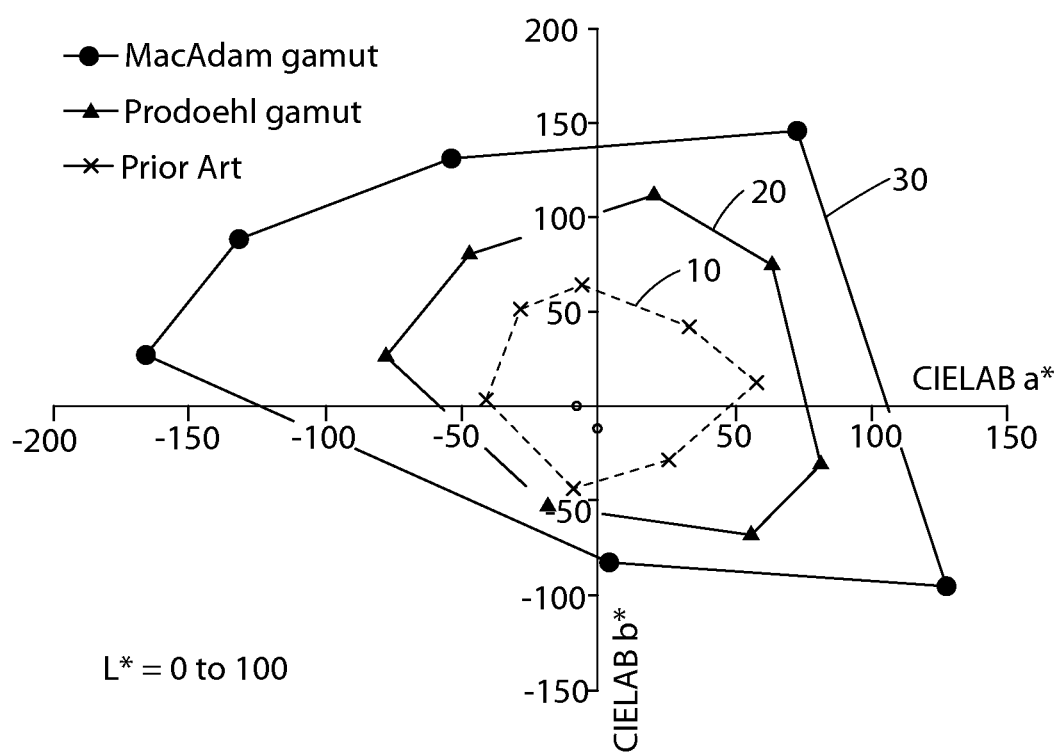
FIG. 1 is a graphical representation of exemplary extrapolated MacAdam, Prodoehl, and Kien 2-D color gamuts in CIELab (L*a*b*) coordinates showing the a*b* plane where L*=0 to 100.

"Absorbent paper product," as used herein, refers to products comprising paper tissue or paper towel technology in general, including, but not limited to, conventional felt-pressed or conventional wet-pressed fibrous structure product, pattern densified fibrous structure product, starch substrates, and high bulk, un-compacted fibrous structure product. Non-limiting examples of tissue-towel paper products include intentionally absorbent disposable or reusable, paper toweling, facial tissue, bath tissue, and the like. In one non-limiting embodiment, the absorbent paper product is directed to a paper towel product. In another non-limiting embodiment, the absorbent paper product is directed to a rolled paper towel product. One of skill in the art will appreciate that in one embodiment an absorbent paper product may have CD and/or MD modulus properties and/or stretch properties that are different from other printable substrates, such as card paper. Such properties may have important implications regarding the absorbency and/or roll-ability of the product. Such properties are described in greater detail infra.

In one embodiment, an absorbent paper product substrate may be manufactured via a wet-laid paper making process. In other embodiments, the absorbent paper product substrate may be manufactured via a through-air-dried paper making process or foreshortened by creping or by wet micro-contraction. In some embodiments, the resultant paper product plies may be differential density fibrous structure plies, wet laid fibrous structure plies, air laid fibrous structure plies, conventional fibrous structure plies, and combinations thereof. Creping and/or wet micro-contraction are disclosed in U.S. Pat. Nos. 6,048,938, 5,942,085, 5,865,950, 4,440,597, 4,191,756, and 6,187,138.

In an embodiment, the absorbent paper product may have a texture imparted into the surface thereof wherein the texture is formed into product during the wet-end of the papermaking process using a patterned papermaking belt. Exemplary processes for making a so-called pattern densified absorbent paper product include, but are not limited to, those processes disclosed in U.S. Pat. Nos. 3,301,746, 3,974,025, 4,191,609, 4,637,859, 3,301,746, 3,821,068, 3,974,025, 3,573,164, 3,473,576, 4,239,065, and 4,528,239.

In other embodiments, the absorbent paper product may be made using a through-air-dried (TAD) substrate. Examples of, processes to make, and/or apparatus for making through air dried paper are described in U.S. Pat. Nos. 4,529,480, 4,529,480, 4,637,859, 5,364,504, 5,529,664, 5,679,222, 5,714,041, 5,906,710, 5,429,686, and 5,672,248.

In other embodiments still, the absorbent paper product substrate may be conventionally dried with a texture as is described in U.S. Pat. Nos. 5,549,790, 5,556,509, 5,580,423, 5,609,725, 5,629,052, 5,637,194, 5,674,663, 5,693,187, 5,709,775, 5,776,307, 5,795,440, 5,814,190, 5,817,377, 5,846,379, 5,855,739, 5,861,082, 5,871,887, 5,897,745, and 5,904,811.

"Base Color," as used herein, refers to a color that is used in the halftoning printing process as the foundation for creating additional colors. In some non-limiting embodiments, a base color is provided by a colored ink and/or dye. Non-limiting examples of base colors may selected from the group consisting of: cyan, magenta, yellow, black, red, green, and blue-violet.

"Basis Weight", as used herein, is the weight per unit area of a sample reported in lbs/3000 ft$^2$ or g/m$^2$.

"Black", as used herein, refers to a color and/or base color which absorbs wavelengths in the entire spectral region of from about 380 nm to about 740 nm.

"Blue" or "Blue-violet", as used herein, refers to a color and/or base color which have a local maximum reflectance in the spectral region of from about 390 nm to about 490 nm.

"Cyan", as used herein, refers to a color and/or base color which have a local maximum reflectance in the spectral region of from about 390 nm to about 570 nm. In some embodiments, the local maximum reflectance is between the local maximum reflectance of the blue or blue-violet and green local maxima.

"Cross Machine Direction" or "CD", as used herein, means the direction perpendicular to the machine direction in the same plane of the fibrous structure and/or fibrous structure product comprising the fibrous structure.

"Densified", as used herein, means a portion of a fibrous structure product that exhibits a greater density than another portion of the fibrous structure product.

"Dot gain" is a phenomenon in printing which causes printed material to look darker than intended. It is caused by halftone dots growing in area between the original image ("input halftone") and the image finally printed upon the web material ("output halftone").

A "dye" is a liquid containing coloring matter, for imparting a particular hue to cloth, paper, etc. For purposes of clarity, the terms "fluid" and/or "ink" and/or "dye" may be used interchangeably herein and should not be construed as limiting any disclosure herein to solely a "fluid" and/or "ink" and/or "dye."

"Fiber" means an elongate particulate having an apparent length greatly exceeding its apparent width. More specifically, and as used herein, fiber refers to such fibers suitable for a papermaking process. The present invention contemplates the use of a variety of paper making fibers, such as, natural fibers, synthetic fibers, as well as any other suitable fibers, starches, and combinations thereof. Paper making fibers useful in the present invention include cellulosic fibers commonly known as wood pulp fibers. Applicable wood pulps include chemical pulps, such as Kraft, sulfite and sulfate pulps; mechanical pulps including groundwood, thermomechanical pulp; chemithermomechanical pulp; chemically modified pulps, and the like. Chemical pulps, however, may be preferred in tissue towel embodiments since they are known to those of skill in the art to impart a superior tactical sense of softness to tissue sheets made therefrom. Pulps derived from deciduous trees (hardwood) and/or coniferous trees (softwood) can be utilized herein. Such hardwood and softwood fibers can be blended or deposited in layers to provide a stratified web. Exemplary layering embodiments and processes of layering are disclosed in U.S. Pat. Nos. 3,994,771 and 4,300,981. Additionally, fibers derived from non-wood pulp such as cotton linters, bagesse, and the like, can be used. Additionally, fibers derived from recycled paper, which may contain any or all of the pulp categories listed above, as well as other non-fibrous materials such as fillers and adhesives used to manufacture the original paper product may be used in the present web.

In addition, fibers and/or filaments made from polymers, specifically hydroxyl polymers, may be used in the present invention. Non-limiting examples of suitable hydroxyl polymers include polyvinyl alcohol, starch, starch derivatives, chitosan, chitosan derivatives, cellulose derivatives, gums, arabinans, galactans, and combinations thereof. Additionally, other synthetic fibers such as rayon, lyocel, polyester, polyethylene, and polypropylene fibers can be used within the scope of the present invention. Further, such fibers may be latex bonded.

"Fibrous structure," as used herein, means an arrangement of fibers produced in any papermaking machine known in the art to create a ply of paper product or absorbent paper product. Other materials are also intended to be within the scope of the present invention as long as they do not interfere or counter act any advantage presented by the instant invention. Suitable materials may include foils, polymer sheets, cloth, wovens or nonwovens, paper, cellulose fiber sheets, co-extrusions, laminates, high internal phase emulsion foam materials, and combinations thereof. The properties of a selected deformable material can include, though are not restricted to, combinations or degrees of being: porous, non-porous, microporous, gas or liquid permeable, non-permeable, hydrophilic, hydrophobic, hydroscopic, oleophilic, oleophobic, high critical surface tension, low critical surface tension, surface pre-textured, elastically yieldable, plastically yieldable, electrically conductive, and electrically non-conductive. Such materials can be homogeneous or composition combinations.

A "fluid" is a substance, as a liquid or gas, that is capable of flowing and that changes its shape at a steady rate when acted upon by a force tending to change its shape. Exemplary fluids suitable for use with the present disclosure includes inks, dyes, softening agents, cleaning agents, dermatological solutions, wetness indicators, adhesives, combinations thereof, and the like.

"Green", as used herein, refers to a color and/or base color which have a local maximum reflectance in the spectral region of from about 491 nm to about 570 nm.

"Halftone" or "halftoning" as used herein, sometimes known to those of skill in the printing arts as "screening," is a printing technique that allows for less-than-full saturation of the primary colors. In halftoning, relatively small dots of each primary color are printed in a pattern small enough such that the average human observer perceives a single color. For example, magenta printed with a 20% halftone will appear to the average observer as the color pink. The reason for this is because, without wishing to be limited by theory, the average observer may perceive the tiny magenta dots and white paper between the dots as lighter, and less saturated, than the color of pure magenta ink.

"Hue" is the relative red, yellow, green, and blue-violet in a particular color. A ray can be created from the origin to any color within the two-dimensional a*b* space. Hue is the angle measured from 0° (the positive a* axis) to the created ray. Hue can be any value of between 0° to 360°. Lightness is determined from the L* value with higher values being more white and lower values being more black.

An "ink" is a fluid or viscous substance used for writing or printing.

"Lab Color" or "L*a*b* Color Space," as used herein, refers to a color model that is used by those of skill in the art to characterize and quantitatively describe perceived colors with a relatively high level of precision. More specifically, CIELab may be used to illustrate a gamut of color because L*a*b* color space has a relatively high degree of perceptual uniformity between colors. As a result, L*a*b* color space may be used to describe the gamut of colors that an ordinary observer may actually perceive visually.

A color's identification is determined according to the Commission Internationale de l'Eclairage L*a*b* Color Space (hereinafter "CIELab"). CIELab is a mathematical color scale based on the Commission Internationale de l'Eclairage (hereinafter "CIE") 1976 standard. CIELab allows a color to be plotted in a three-dimensional space analogous to the Cartesian xyz space. Any color may be plotted in CIELab according to the three values (L*, a*, b*). For example, there is an origin with two axis a* and b* that are coplanar and perpendicular, as well as an L-axis which is perpendicular to the a* and b* axes, and intersects those axes only at the origin. A negative a* value represents green and a positive a* value represents red. CIELab has the colors blue-violet to yellow on what is traditionally the y-axis in Cartesian xyz space. CIELab identifies this axis as the b*-axis. Negative b* values represent blue-violet and positive b* values represent yellow. CIELab has lightness on what is traditionally the z-axis in Cartesian xyz space. CIELab identifies this axis as the L-axis. The L*-axis ranges in value from 100, which is white, to 0, which is black. An L* value of 50 represents a mid-tone gray (provided that a* and b* are 0). Any color may be plotted in CIELab according to the three values (L*, a*, b*). As described supra, equal distances in CIELab space correspond to approximately uniform changes in perceived color. As a result, one of skill in the art is able to approximate perceptual differences between any two colors by treating each color as a different point in a three dimensional, Euclidian, coordinate system, and calculating the Euclidian distance between the two points ($\Delta E^*_{ab}$).

The three dimensional CIELab allows the three color components of chroma, hue, and lightness to be calculated. Within the two-dimensional space formed from the a-axis and b-axis, the components of hue and chroma can be determined. Chroma, (C*), is the relative saturation of the perceived color and can be determined by the distance from the origin in the a*b* plane. Chroma, for a particular a*, b* set can be calculated as follows:

$$C^* = (a^{*2} + b^{*2})^{1/2}$$

For example, a color with a*b* values of (10,0) would exhibit a lesser chroma than a color with a*b* values of (20,0). The latter color would be perceived qualitatively as being "more red" than the former. Hue is the relative red, yellow, green, and blue-violet in a particular color. A ray can be created from the origin to any color within the two-dimensional a*b* space.

"Machine Direction" or "MD", as used herein, means the direction parallel to the flow of the fibrous structure through the papermaking machine and/or product manufacturing equipment.

"Magenta", as used herein, refers to a color and/or base color which have a local maximum reflectance in the spectral region of from about 390 nm to about 490 nm and 621 nm to about 740 nm.

"Modulus", as used herein, is a stress-strain measurement which describes the amount of force (or pressure) required to deform a material at a given point.

"Paper product," as used herein, refers to any formed, fibrous structure products, traditionally, but not necessarily, comprising cellulose fibers. In one embodiment, the paper products of the present invention include tissue-towel paper products.

"Ply" or "plies," as used herein, means an individual fibrous structure, sheet of fibrous structure, or sheet of an absorbent paper product optionally to be disposed in a substantially contiguous, face-to-face relationship with other plies, forming a multi-ply fibrous structure. It is also contemplated that a single fibrous structure can effectively form two "plies" or multiple "plies", for example, by being folded on itself. In one embodiment, the ply has an end use as a tissue-towel paper product. A ply may comprise one or more wet-laid layers, air-laid layers, and/or combinations thereof. If more than one layer is used, it is not necessary for each layer to be made from the same fibrous structure. Further, the layers may or may not be homogenous within a layer. The actual makeup of a fibrous structure product ply is generally determined by the desired benefits of the final tissue-towel paper product, as would be known to one of skill in the art. The fibrous structure may comprise one or more plies of non-woven materials in addition to the wet-laid and/or air-laid plies.

"Process Printing," as used herein, refers to the method of providing color prints using three primary colors cyan, magenta, yellow and black. Each layer of color is added over a base substrate. In some embodiments, the base substrate is white or off-white in color. With the addition of each layer of color, certain amounts of light are absorbed (those of skill in the printing arts will understand that the inks actually "subtract" from the brightness of the white background), resulting in various colors. CMY (cyan, magenta, yellow) are used in combination to provide additional colors. Non-limiting examples of such colors are red, green, and blue. K (black) is used to provide alternate shades and pigments. One of skill in the art will appreciate that CMY may alternatively be used in combination to provide a black-type color.

"Red", as used herein, refers to a color and/or base color which has a local maximum reflectance in the spectral region of from about 621 nm to about 740 nm.

"Resultant Color," as used herein, refers to the color that an ordinary observer perceives on the finished product of a halftone printing process. As exemplified supra, the resultant color of magenta printed at a 20% halftone is pink.

"Sanitary tissue product", as used herein, means one or more fibrous structures, converted or not, that is useful as a wiping implement for post-urinary and post-bowel movement cleaning (bath tissue), for otorhinolaryngological discharges (facial tissue and/or disposable handkerchiefs), and multi-functional absorbent and cleaning uses (absorbent towels and/or wipes).

"Sheet caliper" or "caliper", as used herein, means the macroscopic thickness of a sample.

"Stretch", as used herein, is determined by measuring a fibrous structure's dry tensile strength in the MD and/or CD.

As used herein, the terms "tissue paper web, paper web, web, paper sheet and paper product" are all used interchangeably to refer to sheets of paper made by a process comprising the steps of forming an aqueous papermaking furnish, depositing this furnish on a foraminous surface, such as a Fourdrinier wire, and removing the water from the furnish (e.g., by gravity or vacuum-assisted drainage), forming an embryonic web, transferring the embryonic web from the forming surface to a transfer surface traveling at a lower speed than the forming surface. The web is then transferred to a fabric upon which it is through air dried to a final dryness after which it is wound upon a reel.

"User contacting surface", as used herein, means that portion of the fibrous structure and/or surface treating composition and/or lotion composition that is present directly and/or indirectly on the surface of the fibrous structure that is exposed to the external environment. In other words, it is the surface formed by the fibrous structure including any surface treating composition and/or lotion composition present directly and/or indirectly of the surface of the fibrous structure that can contact an opposing surface during use.

The user contacting surface may be present on the fibrous structure and/or sanitary tissue product for the use by the user and/or user contacting surface may be created/formed prior to and/or during the use of the fibrous structure and/or sanitary tissue product by the user. This may occur by the user applying pressure to the fibrous structure and/or sanitary tissue product as the user contact the user's skin with the fibrous structure and/or sanitary tissue product.

"Web materials" include products suitable for the manufacture of articles upon which indicia may be imprinted thereon and substantially affixed thereto. Web materials suitable for use and within the intended disclosure include fibrous structures, absorbent paper products, and/or products containing fibers. Other materials are also intended to be within the scope of the present invention as long as they do not interfere or counteract any advantage presented by the instant invention. Suitable web materials may include foils, polymer sheets, cloth, wovens or nonwovens, paper, cellulose fiber sheets, co-extrusions, laminates, high internal phase emulsion foam materials, and combinations thereof. The properties of a selected deformable material can include, though are not restricted to, combinations or degrees of being: porous, non-porous, microporous, gas or liquid permeable, non-permeable, hydrophilic, hydrophobic, hydroscopic, oleophilic, oleophobic, high critical surface tension, low critical surface tension, surface pre-textured, elastically yieldable, plastically yieldable, electrically conductive, and electrically non-conductive. Such materials can be homogeneous or composition combinations.

Web materials also include products suitable for use as packaging materials. This may include, but not be limited to, polyethylene films, polypropylene films, liner board, paperboard, cartoning materials, and the like. Additionally, web materials may include absorbent articles (e.g., diapers and catamenial devices). In the context of absorbent articles in the form of diapers, printed web materials may be used to produce components such as backsheets, topsheets, landing zones, fasteners, ears, side panels, absorbent cores, and acquisition layers. Descriptions of absorbent articles and components thereof can be found in U.S. Pat. Nos. 5,569,234; 5,702,551; 5,643,588; 5,674,216; 5,897,545; and 6,120,489; and U.S. Patent Publication Nos. 2010/0300309 and 2010/0089264.

"Wet burst strength", as used herein, is a measure of the ability of a fibrous structure and/or a fibrous structure product incorporating a fibrous structure to absorb energy when wet and subjected to deformation normal to the plane of the fibrous structure and/or fibrous structure product.

"Yellow", as used herein, refers to a color and/or base color which have a local maximum reflectance in the spectral region of from about 571 nm to about 620 nm.

"Z-direction" as used herein, is the direction perpendicular to both the machine and cross machine directions.

All percentages and ratios are calculated by weight unless otherwise indicated. Furthermore, all percentages and ratios are calculated based on the total composition unless otherwise stated. Additionally, unless otherwise noted, all component or composition levels are in reference to the active level of that component or composition and are exclusive of impurities; for example, residual solvents or by-products which may be present in commercially available sources.

Fibrous Structures

The fibrous structure of the present invention preferably further comprises papermaking fibers of both hardwood and softwood types wherein at least about 50% of the papermaking fibers are hardwood and at least about 10% are softwood. The hardwood and softwood fibers are most preferably isolated by relegating each to separate layers wherein the tissue comprises an inner layer and at least one outer layer.

It is anticipated that wood pulp in all its varieties will normally comprise the tissue papers with utility in this invention. However, other cellulose fibrous pulps, such as cotton linters, bagasse, rayon, etc., can be used and none are disclaimed. Wood pulps useful herein include chemical pulps such as, sulfite and sulfate (sometimes called Kraft) pulps as well as mechanical pulps including for example, ground wood, ThermoMechanical Pulp (TMP) and ChemiThermoMechanical Pulp (CTMP). Pulps derived from both deciduous and coniferous trees can be used.

Hardwood pulps and softwood pulps, as well as combinations of the two, may be employed as papermaking fibers for the tissue paper of the present invention. The term "hardwood pulps" as used herein refers to fibrous pulp derived from the woody substance of deciduous trees (angiosperms), whereas "softwood pulps" are fibrous pulps derived from the woody substance of coniferous trees (gymnosperms). Blends of hardwood Kraft pulps, especially eucalyptus, and northern softwood Kraft (NSK) pulps are particularly suitable for making the tissue webs of the present invention. A preferred embodiment of the present invention comprises the use of layered tissue webs wherein, most preferably, hardwood pulps such as eucalyptus are used for outer layer(s) and wherein northern softwood Kraft pulps are used for the inner layer(s). Also applicable to the present invention are fibers derived from recycled paper, which may contain any or all of the above categories of fibers.

In one preferred embodiment of the present invention, which utilizes multiple papermaking furnishes, the furnish containing the papermaking fibers which will be contacted by the particulate filler is predominantly of the hardwood type, preferably of content of at least about 80% hardwood.

Papermaking Process

In one embodiment, the absorbent paper product substrate may be manufactured via a wet-laid paper making process. In other embodiments, the absorbent paper product substrate may be manufactured via a through-air-dried paper making process or foreshortened by creping or by wet micro-contraction. In some embodiments, the resultant paper product plies may be differential density fibrous structure plies, wet laid fibrous structure plies, air laid fibrous structure plies, conventional fibrous structure plies, and combinations thereof.

In an embodiment, the absorbent paper product may have a texture imparted into the surface thereof wherein the texture is formed into the product during the wet-end of the papermaking process using a patterned papermaking belt. Exemplary processes for making a so-called pattern densified absorbent paper product include, but are not limited to, those processes disclosed in U.S. Pat. Nos. 3,301,746, 3,974,025, 4,191,609, 4,637,859, 3,301,746, 3,821,068, 3,974,025, 3,573,164, 3,473,576, 4,239,065, and 4,528,239.

In other embodiments, the absorbent paper product may be made using a through-air-dried (TAD) substrate. Examples of, processes to make, and/or apparatus for making through air dried paper are described in U.S. Pat. Nos. 4,529,480, 4,529,480, 4,637,859, 5,364,504, 5,529,664, 5,679,222, 5,714,041, 5,906,710, 5,429,686, and 5,672,248.

In other embodiments still, the absorbent paper product substrate may be conventionally dried with a texture as is described in U.S. Pat. Nos. 5,549,790, 5,556,509, 5,580,423, 5,609,725, 5,629,052, 5,637,194, 5,674,663, 5,693,187, 5,709,775, 5,776,307, 5,795,440, 5,814,190, 5,817,377, 5,846,379, 5,855,739, 5,861,082, 5,871,887, 5,897,745, and 5,904,811.

The fibrous structure may comprise a ply, or plies, of fibrous structures selected from the group consisting of through-air dried fibrous structure plies, differential density fiber structure plies, wet-laid fibrous structure plies, air-laid fibrous structure plies, conventional fiber structure plies, and combinations thereof. Fibrous structures suitable for use for first ply 12 may comprise identical types of plies or mixtures of different types of plies. Additionally, the fibrous structure may be foreshortened by creping and/or by wet micro-contraction and/or by rush transferring. However, as would be known to one of skill in the art, the fibrous structure may not be foreshortened.

Any compositions present on the surface of the fibrous structure may be present on the surface of the fibrous structure in the form of a pattern such that they cover less than the entire surface area of the surface of the fibrous structure. Alternatively, any compositions present on the surface of the fibrous structure may cover the entire, or substantially the entire surface.

The fibrous structure of the present invention is preferably creped, i.e., produced on a papermaking machine culminating with a Yankee dryer to which a partially dried papermaking web is adhered and upon which it is dried and from which it is removed by the action of a flexible creping blade.

Creping is a means of mechanically compacting paper in the machine direction. The result is an increase in basis weight (mass per unit area) as well as dramatic changes in many physical properties, particularly when measured in the machine direction. Creping is generally accomplished with a flexible blade, a so-called doctor blade, against a Yankee dryer in an on machine operation. Creping and/or wet micro-contraction are disclosed in U.S. Pat. Nos. 6,048,938, 5,942,085, 5,865,950, 4,440,597, 4,191,756, and 6,187,138.

A Yankee dryer is a large diameter, generally 8-20 foot drum which is designed to be pressurized with steam to provide a hot surface for completing the drying of papermaking webs at the end of the papermaking process. The fibrous structure which is first formed on a foraminous forming carrier, such as a Fourdrinier wire, where it is freed of the copious water needed to disperse the fibrous slurry is generally transferred to a felt or fabric in a so-called press section where de-watering is continued either by mechanically compacting the fibrous structure or by some other de-watering method such as through-drying with hot air, before finally being transferred in the semi-dry condition to the surface of the Yankee for the drying to be completed.

While the characteristics of the creped fibrous structures, particularly when the creping process is preceded by methods of pattern densification, are preferred for practicing the present invention, un-creped fibrous structures are also a satisfactory substitute and the practice of the present invention using un-creped fibrous structures is specifically incorporated within the scope of the present invention. Un-creped fibrous structures, a term as used herein, refers to the fibrous structure which is non-compressively dried, most preferably by through-drying. Resultant through air dried webs are pattern densified such that zones of relatively high density are dispersed within a high bulk field, including pattern densified tissue wherein zones of relatively high density are continuous and the high bulk field is discrete.

To produce un-creped fibrous structures, an embryonic web is transferred from the foraminous forming carrier upon which it is laid, to a slower moving, high fiber support transfer fabric carrier. The fibrous structure is then transferred to a drying fabric upon which it is dried to a final dryness. Such fibrous structures can offer some advantages in surface smoothness compared to creped paper webs.

Optional Chemical Additives

Fibrous structures are generally comprised essentially of papermaking fibers. Small amounts of chemical functional agents such as wet strength or dry strength binders, retention aids, surfactants, size, chemical softeners, crepe facilitating compositions are frequently included but these are typically only used in minor amounts. The papermaking fibers most frequently used in tissue papers are virgin chemical wood pulps. Additionally, filler materials may also be incorporated into the tissue papers of the present invention.

Other materials can be added to the aqueous papermaking furnish or the embryonic web to impart other characteristics to the product or improve the papermaking process so long as they are compatible with the chemistry of the softening agent and do not significantly and adversely affect the softness, strength, or low dusting character of the present invention. The following materials are expressly included, but their inclusion is not offered to be all-inclusive. Other materials can be included as well so long as they do not interfere or counteract the advantages of the present invention.

A surface treating composition and/or lotion composition may be applied to the surface of the fibrous structure by any suitable means known in the art. This would include any contact or contact-free application suitable for applying a surface treating composition and/or lotion, such as spraying, dipping, padding, printing, slot extruding, in rows or patterns, rotogravure printing, flexographic printing, off-set printing, screen printing, mask or stencil application processes, and combinations thereof. Such surface treating compositions and/or lotions can be applied to the fibrous structure before, concurrently, or after, a lotion composition application to the fibrous structure.

By way of example, a surface treating composition and/or lotion composition may be applied to the surface of the fibrous structure during the fibrous structure making process, such as before and/or after drying the fibrous structure. Alternatively, a surface treating composition and/or lotion composition may be applied to the surface of the fibrous structure during a converting process.

Softening agents such as quaternary ammonium compounds can be added to the papermaking slurry. Preferred exemplary quaternary compounds include the well-known dialkyldimethylammonium salts (e.g. ditallowedimethylammonium chloride, ditallowedimethylammonium methyl sulfate, di(hydrogenated tallow)dimethyl ammonium chloride, etc.). Further, the mono- or di-ester variations of these quaternary ammonium compounds may be suitable. Specific examples of ester-functional quaternary ammonium compounds having the structures detailed above and suitable for use in the present invention may include the diester dialkyl dimethyl ammonium salts such as diester ditallow dimethyl ammonium chloride, monoester ditallow dimethyl ammonium chloride, diester ditallow dimethyl ammonium methyl sulfate, diester di(hydrogenated)tallow dimethyl ammonium methyl sulfate, diester di(hydrogenated)tallow dimethyl ammonium chloride, and mixtures thereof. Diester ditallow dimethyl ammonium chloride and diester di(hydrogenated) tallow dimethyl ammonium chloride are particularly preferred. These particular materials are available commercially from Witco Chemical Company Inc. of Dublin, Ohio under the tradename "ADOGEN SDMC". Exemplary, quaternary ammonium compounds for use in the present invention are described in U.S. Pat. Nos. 5,543,067; 5,538,595; 5,510,000; 5,415,737, and European Patent Application No. 0 688 901 A2.

Additionally, chemical softening agents suitable for addition to the papermaking slurry comprise well-known organo-reactive polydimethyl siloxane ingredients, including the most preferred—amino functional polydimethyl siloxane. Polysiloxanes which are applicable to chemical softening compositions include polymeric, oligomeric, copolymeric, and other multiple monomeric siloxane materials. As used herein, the term polysiloxane shall include all of such polymeric, oligomeric, copolymeric, and other multiple-monomeric materials. Additionally, the polysiloxane can be straight chained, branched chain, or have a cyclic structure. References disclosing polysiloxanes include U.S. Pat. Nos. 2,826,551; 3,964,500; 4,364,837; 5,059,282; 5,529,665; 5,552,020; and British Patent 849,433.

If permanent wet strength is desired, the group of chemicals: including polyamide-epichlorohydrin, polyacrylamides, styrene-butadiene latices; insolubilized polyvinyl alcohol; urea-formaldehyde; polyethyleneimine; chitosan polymers and mixtures thereof can be added to the papermaking furnish or to the embryonic web. Polyamide-epichlorohydrin resins are cationic wet strength resins which have been found to be of particular utility. Suitable types of such resins are described in U.S. Pat. Nos. 3,700,623 and 3,772,076. One commercial source of useful polyamide-epichlorohydrin resins is Hercules, Inc. of Wilmington, Del., which markets such resin under the mark Kymene 557H®).

Many paper products must have limited strength when wet because of the need to dispose of them through toilets into septic or sewer systems. If wet strength is imparted to these products, it is preferred to be fugitive wet strength characterized by a decay of part or all of its potency upon standing in presence of water. If fugitive wet strength is desired, the binder materials can be chosen from the group consisting of dialdehyde starch or other resins with aldehyde functionality such as Co-Bond 1000® offered by National Starch and Chemical Company, Parez 750® offered by Cytec of Stamford, Conn. and the resin described in U.S. Pat. No. 4,981,557.

If enhanced absorbency is needed, surfactants may be used to treat the tissue paper webs of the present invention. The level of surfactant, if used, is preferably from about 0.01% to about 2.0% by weight, based on the dry fiber weight of the tissue paper. The surfactants preferably have alkyl chains with eight or more carbon atoms. Exemplary anionic surfactants are linear alkyl sulfonates, and alkylbenzene sulfonates. Exemplary nonionic surfactants are alkylglycosides including alkylglycoside esters such as Crodesta SL-40® which is available from Croda, Inc. (New York, N.Y.); alkylglycoside ethers as described in U.S. Pat. No. 4,011,389, issued to W. K. Langdon, et al. on Mar. 8, 1977; and alkylpolyethoxylated esters such as Pegosperse 200 ML available from Glyco Chemicals, Inc. (Greenwich, Conn.) and IGEPAL RC-520® available from Rhone Poulenc Corporation (Cranbury, N.J.).

The present invention is further applicable to the production of multi-layered fibrous webs. Multi-layered fibrous webs and methods of forming multi-layered fibrous webs are described in U.S. Pat. Nos. 3,994,771; 4,300,981; 4,166,001; and European Patent Publication No. 0 613 979 A1. The layers preferably comprise different fiber types, the fibers typically being relatively long softwood and relatively short hardwood fibers as used in multi-layered tissue paper making. Multi-layered tissue paper webs resultant from the present invention comprise at least two superposed layers, an inner layer and at least one outer layer contiguous with the inner layer. Preferably, the multi-layered tissue papers comprise three superposed layers, an inner or center layer, and two outer layers, with the inner layer located between the two outer layers. The two outer layers preferably comprise a primary filamentary constituent of relatively short paper making fibers having an average fiber length between about 0.5 and about 1.5 mm, preferably less than about 1.0 mm. These short paper making fibers typically comprise hardwood fibers, preferably hardwood Kraft fibers, and most preferably derived from eucalyptus. The inner layer preferably comprises a primary filamentary constituent of relatively long paper making fiber having an average fiber length of least about 2.0 mm. These long paper making fibers are typically softwood fibers, preferably, northern softwood Kraft fibers. Preferably, the majority of the particulate filler of the present invention is contained in at least one of the outer layers of the multi-layered tissue paper web of the present invention. More preferably, the majority of the particulate filler of the present invention is contained in both of the outer layers.

Web Material Products: Printing

As described supra, those of skill in the art will appreciate the especially surprising color palette of the present invention absorbent paper products because those of skill in the art will appreciate that absorbent paper product substrates are relatively difficult to print on. Without wishing to be limited by theory, it is thought that because many absorbent paper product substrates are textured, a relatively high level of pressure must be used to transfer ink to the spaces on the surface of the absorbent paper product substrate. In addition, absorbent paper product substrates tend to have a higher amount of dust that is generated during a printing process, which may cause contamination at high speeds using ordinary printing equipment. Further, because an absorbent paper product substrate tends to be more absorbent than an ordinary printable substrate, there may be a relatively high level of dot gain (the spread of the ink from its initial/intended point of printing to surrounding areas). Those of skill in the art will appreciate that a typical piece of paper that may be used for printing a book will have a dot gain of about 3% to about 4% whereas an absorbent paper product may have a dot gain as high as about 20%. As a result, web materials (such as those commensurate in scope with the present disclosure) are typically unable to balance low intensity and high intensity printing. One of skill in the art will appreciate that the ability to achieve smooth tone gradients over the entire tonal range with currently available printing processes is problematic, especially at low (0% to 20%) and high (70% to 100%) halftone densities. In other words, output halftone density is related to input halftone density with the undesired effect of dot gain upon the web substrate. Thus, web materials are typically found to be devoid of colors within the available color gamut at the low end halftone densities. Additionally, halftone control at the high end of the gamut is reached too early with current printing techniques thereby requiring additional dot gain compensation. One of skill in the art will also appreciate that low-intensity colors often serve as the basis for other colors. Prior art strategies of simply increasing color density are found to actually cause a color to lose its chromaticity, and due to a smaller gamut, are found to require the use of a thicker film, which may lead to drying issues and higher cost.

Thus, it was surprisingly found that the products of the instant disclosure can provide a linear relationship between input halftone density and output halftone density over the entire color gamut. Thus, it is preferred that there is a 1:1 relationship between input halftone density and output halftone density. Expressed mathematically, output halftone density equals input halftone density plus dot gain. Preferably, dot gain is less than 20% or less than 10% or less than 5% or zero.

In addition, it has been surprisingly discovered that, while able to provide impressive results regarding color gamut, many prior art printing methods are unsuitable for use in the absorbent paper product industry due to the relatively low modulus of the absorbent paper product substrates. Put another way, one of skill in the art will appreciate that one cannot simply extend a printing method used for a high modulus substrate (i.e., card stock or newspaper) for a low modulus substrate. Further, prior to the present invention, one of ordinary skill in the art would be dissuaded from printing with additional process colors (especially, RGB—additive colors) over traditional process colors (CMYK) because it is thought that because printed colors are produced by overlaying ink pigments rather than combining different wavelengths of light, by printing red, green, and blue on top of one another, not many colors would be produced. For example, using these colors would not produce yellow. It is for this reason that CMYK (subtractive colors) are used.

Further, the low modulus of absorbent paper product substrates (i.e., the absorbent paper product itself) provides for inconsistencies in the substrate that are relatively noticeable when compared to an ordinary paper substrate (such as that for printing a book or newspaper). As a result, maintaining adequate tension in the web during printing without tearing, shredding, stretching, or deforming, the absorbent paper product substrate provides a challenge to any producer of absorbent paper products having printing thereon. Table 1 shows the MD and CD modulus values at a load of about 15.0 grams:

TABLE 1

Modulus of Different Substrates at 15 g Load

| Product | MD Modulus (g/cm) | CD Modulus (g/cm) |
|---|---|---|
| Absorbent Paper Products (Paper Towels) | | |
| Bounty Basic ® (The Procter & Gamble Company) | 1195 | 1891 |
| Bounty ® (The Procter & Gamble Company) | 3227 | 2074 |
| Oasis ™ (Irving) | 1744 | 2594 |
| Kirkland ™ (Georgia Pacific) | 2025 | 9199 |
| Sam's Club ™/Member's Mark ™ (First Quality) | 1052 | 3410 |
| Kroger ™ (Potlatch) | 1653 | 3164 |
| Oasis ™ (First Quality) | 831 | 2279 |
| Sparkle ® (Georgia Pacific) | 2389 | 5143 |
| Scott ® (Kimberly Clark) | 1406 | 1469 |
| Viva ® (Kimberly Clark) | 623 | 604 |
| Ordinary Printable Substrates | | |
| Hallmark ® 2-ply Balloon Napkins (Printed Party Napkin) | 21500 | 36772 |
| Pampers ® Feel and Learn 26-count Package (Polyethylene Wrapper/Flexible Packaging) | 23382 | 25351 |

TABLE 1-continued

Modulus of Different Substrates at 15 g Load

| Product | MD Modulus (g/cm) | CD Modulus (g/cm) |
|---|---|---|
| Aug. 8, 2007 USA Today (Newspaper) | 92828 | 58987 |

In some embodiments of the present invention, the absorbent paper product is a paper towel product, such as those sold under the Bounty® trademark (The Procter and Gamble Co., Cincinnati, Ohio). As exemplified above, absorbent paper products, as contemplated by the present invention, can be distinguished from ordinary printable substrates by the MD and/or CD modulus. In some embodiments, the absorbent paper products of the present invention have a MD and/or CD modulus of less than about 20,000 g/cm at a load of about 15 g. In other embodiments, the absorbent paper products have a MD and/or CD load of from about 500 g/cm to about 20,000 g/cm at a load of about 15 g. In another embodiment, the absorbent paper products have a MD and/or CD load of from about 1000 g/cm to about 15,000 g/cm at a load of about 15 g. In another embodiment still, the absorbent paper products have a MD and/or CD load of from about 2000 g/cm to about 10,000 g/cm at a load of about 15 g. Modulus may be measured according to the Modulus Test Method described below.

As described supra, those of skill in the art will appreciate that printing on absorbent paper product substrate poses additional difficulties compared to ordinary printable substrates. Additional challenges and difficulties associated with printing on paper towel substrates are described in U.S. Pat. No. 6,993,964.

In one embodiment, central impression printing may be used to provide ink to the substrates. Exemplary central impression printing methods and apparatus are described in U.S. Pat. Nos. 6,220,156, 6,283,024, and 5,083,511. In another embodiment, in-line printing may be used to provide ink to the substrates. Exemplary in-line printing methods and apparatus are described in U.S. Pat. Nos. 6,587,133, 6,026,748, and 5,331,890. Printing may also be performed using any multi-stage printing apparatus for printing on absorbent paper product substrates such as those exemplified in U.S. Pat. Nos. 5,638,752, 6,026,748, and 5,331,890.

In one embodiment, the present invention may be performed on a multi-stage printing system. In one embodiment, seven colors can be used to provide the printed substrates of the present disclosure. Surprisingly, it is found that when red, green, and blue-violet inks in particular are used in conjunction with the standard CMYK process colors for a seven-color process printing procedure, the resultant absorbent paper products made with this process/apparatus exhibited a noticeably improved appearance and larger color gamut as compared to the prior art four color printing. Without wishing to be limited by theory, it is thought that the additional ink colors provide a larger resultant color palette than is possible from the prior art printing processes/apparatus. Non-limiting halftoning values are preferably greater than 20 dpi or greater than 50 dpi or greater than 85 dpi or greater than 100 dpi or greater than 150 dpi print resolution for disparate inks disposed adjacent each other upon a web substrate.

Figure 8:
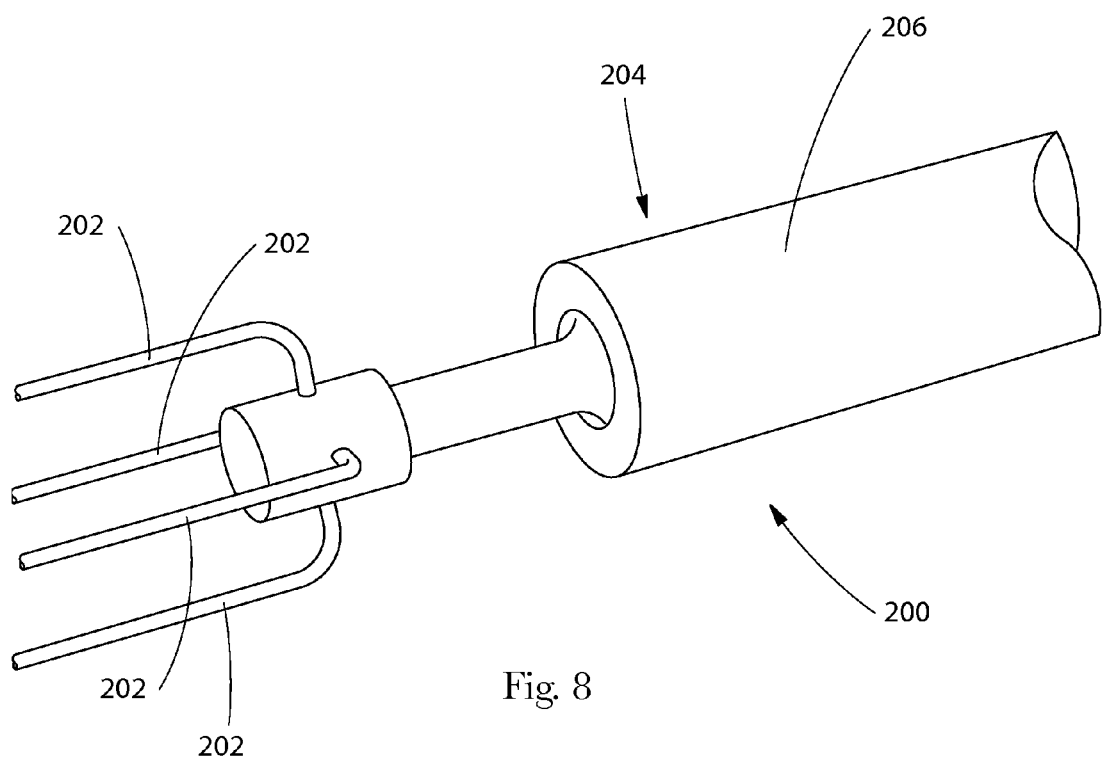
FIG. 8 is a perspective view of an exemplary gravure cylinder suitable for producing the product of the present disclosure.

Alternatively, FIG. 8 shows a perspective view of an exemplary, non-limiting, contact printing system 200. Such contact printing systems 200 can be generally formed from printing components that displace a fluid 202 onto a web substrate or article (also known as a central roll or gravure cylinder 204)

and any other ancillary components necessary to assist the displacement of the fluid 202 from the central roll 204 onto the web substrate or article in order to, for example, print an image onto the web substrate or article. As shown, an exemplary printing component commensurate in scope with the apparatus of the present disclosure can be a gravure cylinder 204 such as a gravure cylinder. The exemplary gravure cylinder 204 is used to carry a desired pattern and quantity of fluid 202 (e.g., ink) and transfer a portion of the fluid 202 to a web material or article that has been placed in contact with the gravure cylinder 204 which in turn transfers the fluid 202 to the web material or article. Alternatively, as would be understood by one of skill in the art, the principles of the present disclosure would also apply to a printing plate which in turn can transfer a fluid 202 to a web material. In any regard, the invention of the present disclosure is ultimately used to apply a broad range of fluids 202 to a web substrate at a target rate and in a desired pattern. By way of non-limiting example, the contact printing system 200 of the present invention incorporating the unique and exemplary gravure cylinder 204 described herein can apply more than just a single fluid 202 (e.g., can apply a plurality of individual inks each having a different color) to a web substrate when compared to a conventional gravure printing system as described supra (e.g., a single central impression cylinder can only apply a single ink). For example, various inks can be mixed in situ to form a virtually unlimited number of colors representing a heretofore unrealizable gamut.

Represented mathematically, the contact printing system 200 of the present invention described herein can print X colors upon a web substrate utilizing X-Y printing components where X and Y are whole numbers, 0<Y<X, and X>1. In a preferred embodiment, each fluid 202 disposed upon a web substrate in contact with the gravure cylinder 204 is first disposed within the inner portion of the gravure cylinder 204 and directed to those portions of the outer surface 206 of gravure cylinder 204 to form the desired pattern of any indicia to be formed upon a web substrate in contact with gravure cylinder 204. Each fluid 202 may be applied directly to a web substrate or can be combined with another fluid (which may or may not be the resulting combination of other different fluids 202) and applied to a web substrate. Such an exemplary contact printing system is described in co-pending U.S. patent application Ser. No. 13/040,287 filed on Mar. 4, 2011 (U.S. Patent Publication Ser. No. 2012/0222567 A1). In a preferred embodiment, the contact printing system 200 can print at least 2 colors with 1 printing component or at least 3 colors with 1 printing component or at least 4 colors with 1 printing component or at least 5 colors with 1 printing component or at least 6 colors with 1 printing component or at least 7 colors with 1 printing component or at least 8 colors with 1 printing component. In alternative embodiment, the contact printing system 200 can print at least 3 colors with 3 printing components or at least 4 colors with 2 printing components or at least 8 colors with 2 printing components or at least 4 colors with 3 printing components or at least 16 colors with 2 printing components or at least 16 colors with 3 printing components or at least 24 colors with 3 printing components.

As described supra, one embodiment of the present disclosure is printed using a greater number of base colors than in any prior art printing processes. In one embodiment, the base colors that can be used are: cyan, magenta, yellow, black, red, green, and blue-violet.

In other embodiments, to improve ink rub-off resistance, the ink composition of this invention may contain a wax. A wax suitable for this invention includes but is not limited to a polyethylene wax emulsion. Addition of a wax to the ink composition of the present invention enhances rub resistance by setting up a barrier which inhibits the physical disruption of the ink film after application of the ink to the fibrous sheet. Based on weight percent solids of the total ink composition, suitable addition ranges for the wax are from about 0.5% solids to 10% solids. An example of a suitable polyethylene wax emulsion is JONWAX 26 supplied by S.C. Johnson & Sons, Inc. of Racine, Wis. Glycerin may also be added to the ink composition used in the present invention in order to improve rub-off resistance. Based upon weight percent of the total ink composition, suitable addition ranges for glycerin can range from about 0.5% to 20%, or from about 3% to 15%, or from about 8% to 13%.

FIG. 1 shows an exemplary extrapolated graphical representation of the 2-dimensional (2-D) color gamut available to the Kien absorbent paper product substrates in an L*a*b color space in the a*b* plane. The L*a*b* points are chosen according to the Color Test Method described below. Without wishing to be limited by theory, it is thought that the most "intense" (i.e., 100% halftone) colors represent the outer boundaries of the color gamut. Surprisingly, it was found that the Kien 2-D color gamut 10 does not occupy as large of an area as the MacAdam 2-D color gamut 30 (the maximum 2-D theoretical human color perception) or the Prodoehl 2-D color gamut 20 (the preferred 2-D surface color gamut) as applied to web substrates of the present disclosure such as absorbent paper products. Stated differently, the combination of the colors available with the MacAdam color gamut 30 and Prodoehl color gamut 20 provided resultant colors that extended beyond the limitations of the red, green, and blue-violet process colors and well beyond the Kien 2-D color gamut 10 colors and color combinations when described in L*a*b* space.

For the 2-D color gamuts discussed supra, the formula (new gamut area—prior art gamut area)/prior art gamut area *100% is used to calculate the percent increase of the area circumscribed by the 2-D gamut plots of the Prodoehl color gamut 20 and the MacAdam color gamut 30 compared to the Kien color gamut 10. The area circumscribed by the Kien color gamut 10, the Prodoehl color gamut 20, and the MacAdam color gamut 30 can be determined to be 6,641, 19,235, and 45,100 relative area units, respectively. Using these values in the equation results in color gamut percentage increases of about 190% (Prodoehl) and about 579% (MacAdam) respectively that are available over the palette of the prior art absorbent paper products—clearly, a surprising result.

Figure 2:
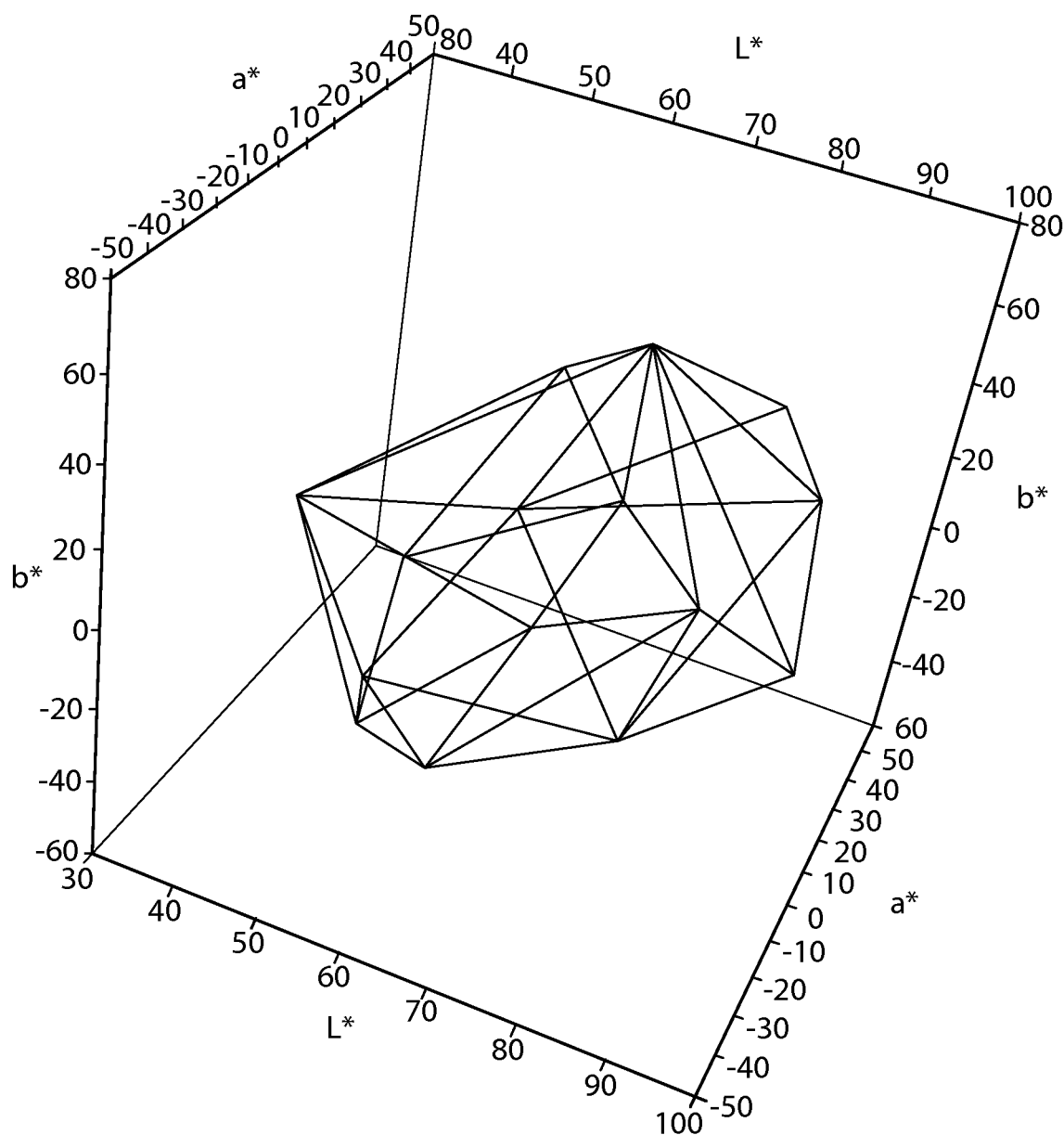
FIG. 2 is a graphical representation of exemplary extrapolated Kien 3-D color gamut in CIELab (L*a*b*) coordinates.
Figure 3:
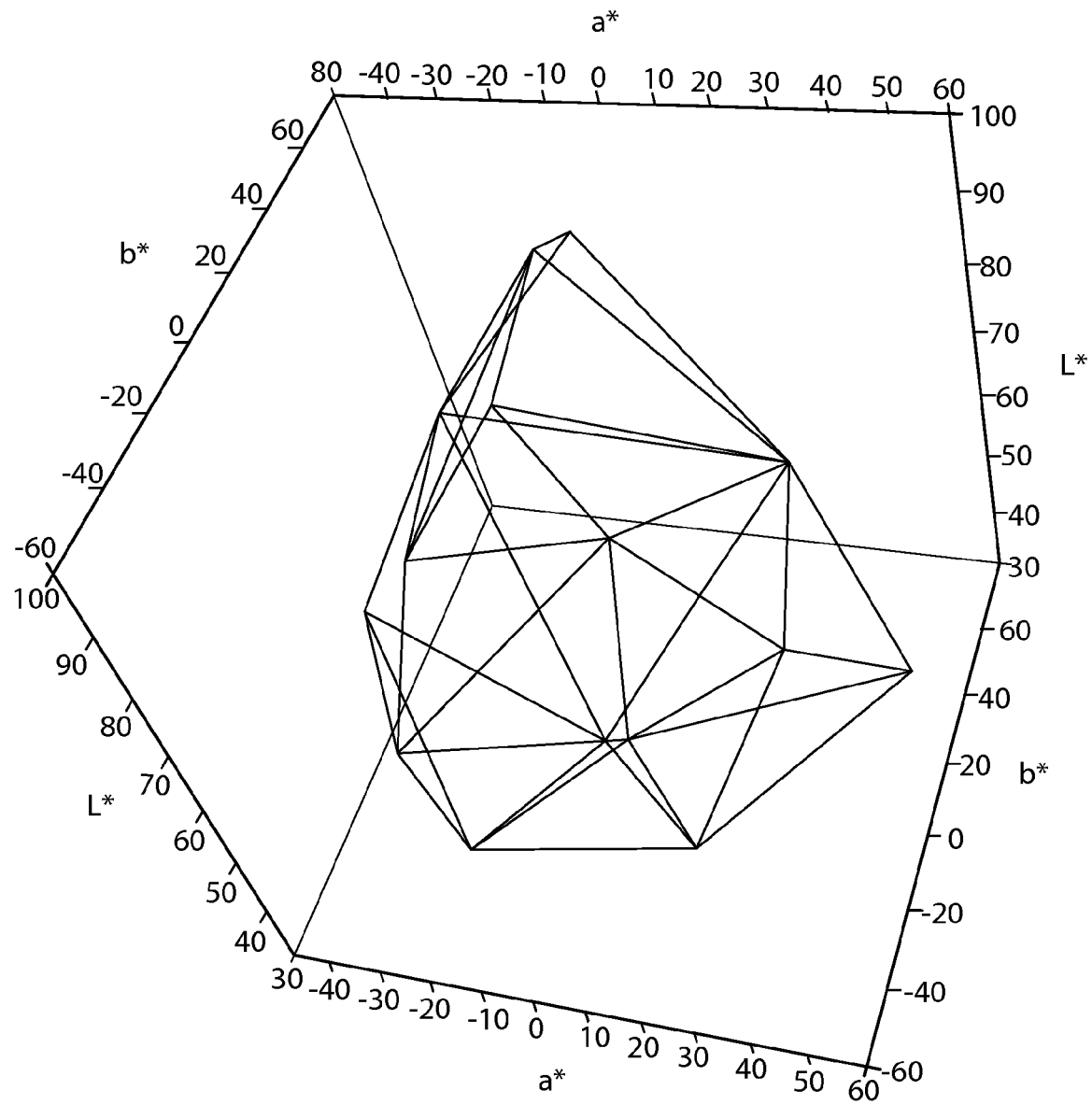
FIG. 3 is an alternative graphical representation of exemplary extrapolated Kien 3-D color gamut in CIELab (L*a*b*) coordinates.

For the 3-D color gamuts discussed supra, the formula (new gamut volume—prior art gamut volume)/prior art gamut volume *100% is used to calculate the percent increase of the volume enveloped by the 3-D gamut plots of the Prodoehl color gamut (FIGS. 6 and 7) (the preferred surface color gamut) and the MacAdam color gamut (FIGS. 4 and 5) (the maximum 3-D theoretical human color perception) compared to the Kien color gamut (FIGS. 2 and 3). The volume enveloped by the Kien 3-D color gamut, the Prodoehl 3-D color gamut, and the MacAdam 3-D color gamut can be determined to be 158,000, 1,234,525, and 2,572,500 relative volume units, respectively. Using these values in the equation results in 3-D color gamut percentage increases of about 681% (Prodoehl) and about 1,528% (MacAdam) respectively that are available over the palette of the prior art absorbent paper products—clearly, a surprising result.

As described supra, it is observed that a product having the herein described increased color gamut are more visually perceptible when compared to products limited by the prior art gamut. This can be particularly true for absorbent paper products using the herein described gamuts. Without desiring to be bound by theory, this can be because there are more visually perceptible colors in the gamuts of the present disclosure. It is surprisingly noticed that the present invention also provides products having a full color scale with no loss in gamut.

The color gamut boundaries in both 2-D CIELab (L*a*b*) space and 3-D CIELab (L*a*b*) space commensurate in scope with the present disclosure may be approximated by the following system of equations in CIELab coordinates (L*a*b) respectively:

MacAdam 2-D Color Gamut $\{a^*=-54.1 \text{ to } 72.7; b^*=131.5 \text{ to } 145.8\} \rightarrow b^*=0.113 a^*+137.6$ $\{a^*=-131.6 \text{ to } -54.1; b^*=89.1 \text{ to } 131.5\} \rightarrow b^*=0.547 a^*+161.1$ $\{a^*=-165.6 \text{ to } -131.6; b^*=28.0 \text{ to } 89.1\} \rightarrow b^*=1.797 a^*+325.6$ $\{a^*=3.6 \text{ to } -165.6; b^*=-82.6 \text{ to } 28.0\} \rightarrow b^*=-0.654 a^*-80.3$ $\{a^*=127.1 \text{ to } 3.6; b^*=-95.1 \text{ to } -82.6\} \rightarrow b^*=-0.101 a^*-82.3$ $\{a^*=-72.7 \text{ to } 127.1; b^*=145.8 \text{ to } -95.1\} \rightarrow b^*=-4.428 a^*+467.7$ where L* ranges from 0 to 100.

Prodoehl 2-D Color Gamut $\{a^*=20.0 \text{ to } 63.6; b^*=113.3 \text{ to } 75.8\} \rightarrow b^*=-0.860 a^*+130.50$ $\{a^*=-47.5 \text{ to } 20.0; b^*=82.3 \text{ to } 113.3\} \rightarrow b^*=0.459 a^*+104.11$ $\{a^*=-78.0 \text{ to } -47.5; b^*=28.4 \text{ to } 82.3\} \rightarrow b^*=1.767 a^*+166.24$ $\{a^*=-18.8 \text{ to } -78.0; b^*=-51.7 \text{ to } 28.4\} \rightarrow b^*=-1.353 a^*-77.14$ $\{a^*=56.6 \text{ to } -18.8; b^*=-67.4 \text{ to } -51.7\} \rightarrow b^*=-0.208 a^*-55.61$ $\{a^*=81.8 \text{ to } 56.6; b^*=-29.8 \text{ to } -67.4\} \rightarrow b^*=1.492 a^*-151.85$ $\{a^*=63.6 \text{ to } 81.8; b^*=75.8 \text{ to } -29.8\} \rightarrow b^*=-5.802 a^*+444.82$ where L* ranges from 0 to 100.

Figure 4:
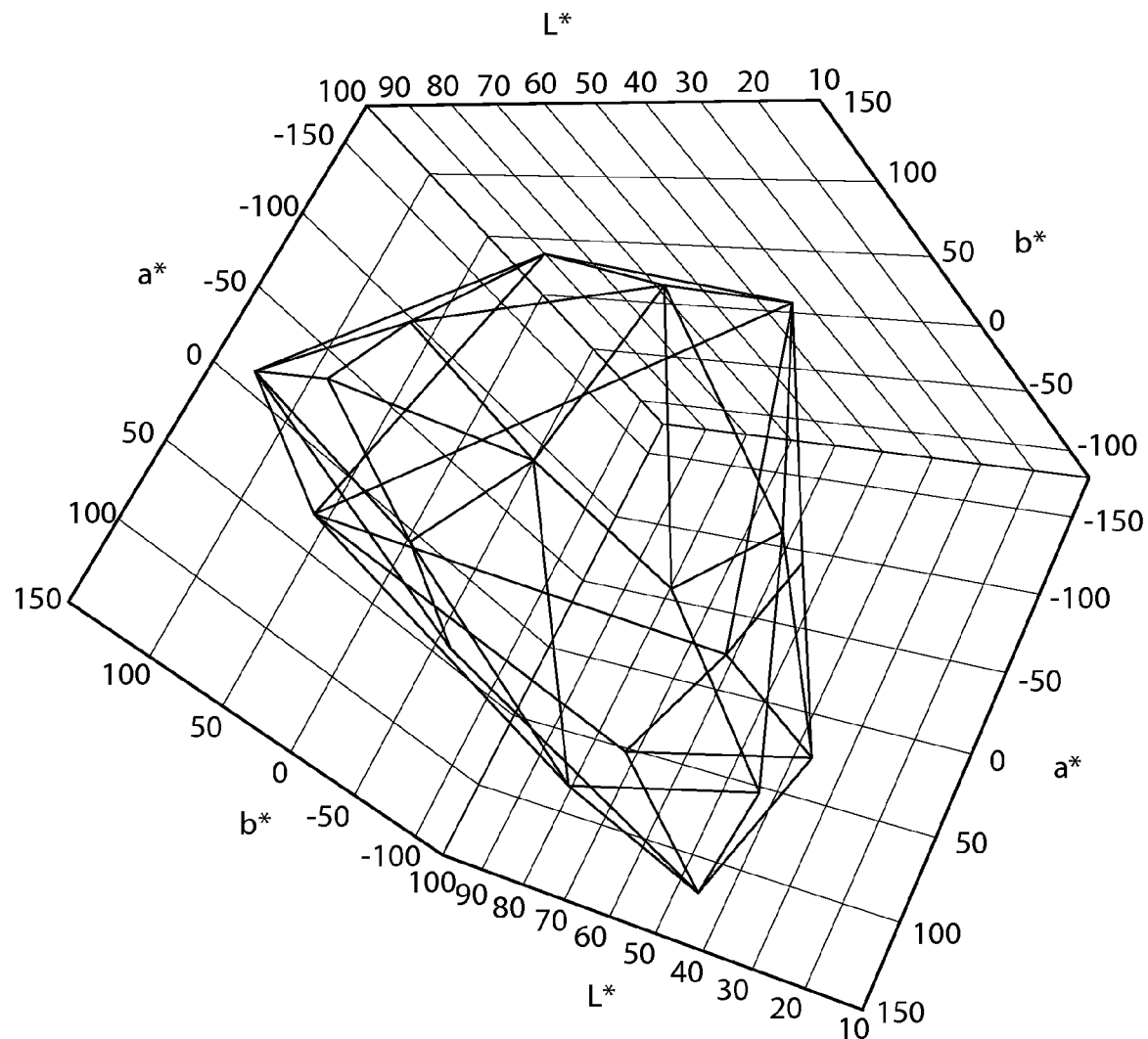
FIG. 4 is a graphical representation of exemplary extrapolated MacAdam 3-D color gamut in CIELab (L*a*b*) coordinates.
Figure 5:
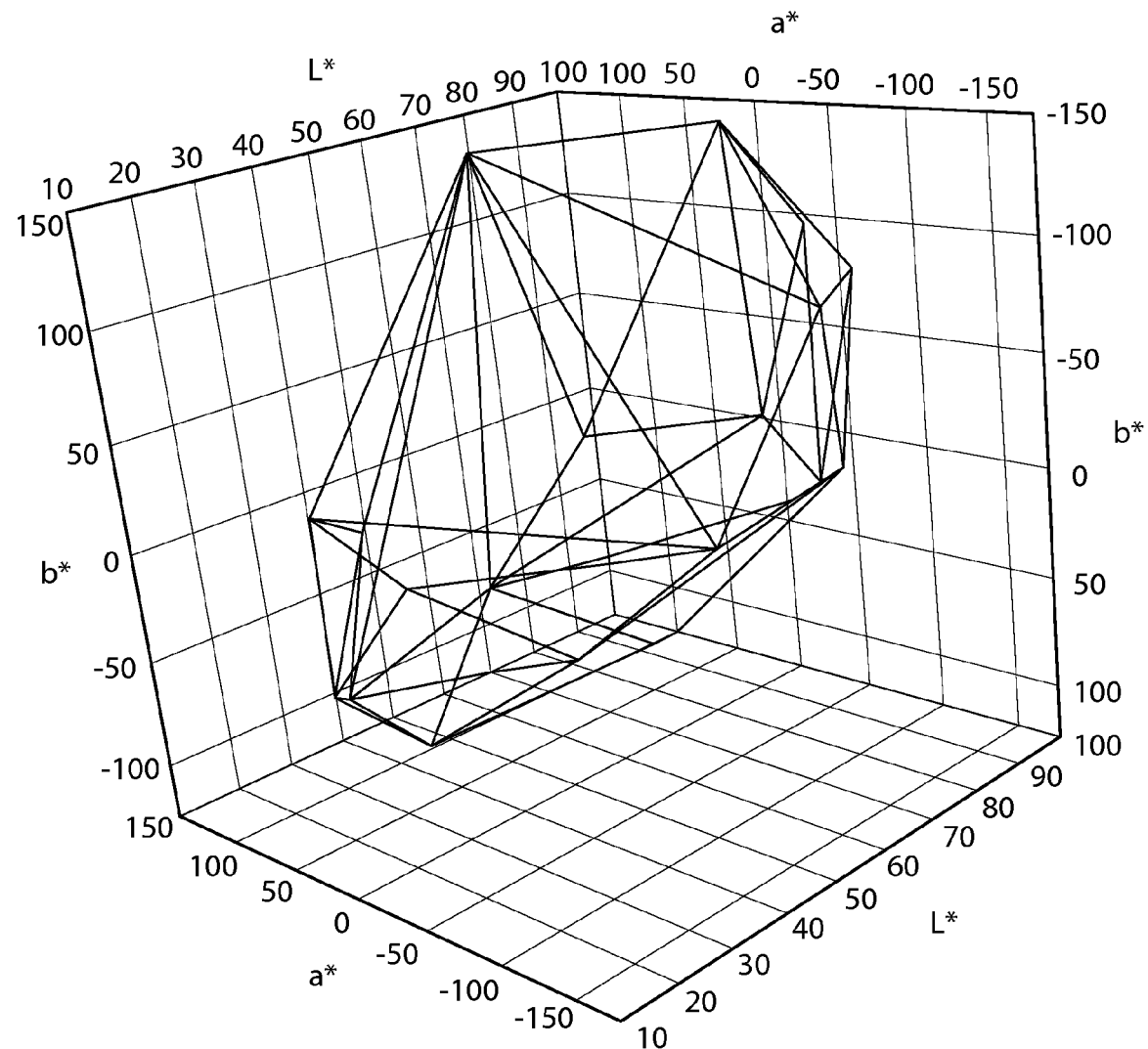
FIG. 5 is an alternative graphical representation of exemplary extrapolated MacAdam 3-D color gamut in CIELab (L*a*b*) coordinates.

MacAdam 3-D Color Gamut (FIGS. 4 and 5)

| Vertexes Defining Each Face | | | | | | | | | E a* + F b* + G L* + H = 0 | | | |
|---|---|---|---|---|---|---|---|---|---|---|---|---|
| Vertex 1 | | | Vertex 2 | | | Vertex 3 | | | Face Plane Equation Coefficients | | | |
| z1 | x1 | y1 | z2 | x2 | y2 | z3 | x3 | y3 | | | | |
| L* | a* | b* | L* | a* | b* | L* | a* | b* | E | F | G | H |
| 20 | 41.6 | 24 | 20 | −24.6 | 4.3 | 20 | 48.9 | −58.2 | 0.0 | 0.0 | 5585.5 | −111709.0 |
| 20 | 41.6 | 24 | 20 | −24.6 | 4.3 | 37.8 | −162 | 25 | −350.7 | 1178.4 | −4077.1 | 67849.2 |
| 20 | 41.6 | 24 | 20 | 48.9 | −58.2 | 37.8 | 92.4 | −8.8 | −1463.2 | −129.9 | 3936.3 | −14740.4 |
| 20 | 41.6 | 24 | 37.8 | 92.4 | −8.8 | 61.7 | 72.7 | 146 | −3535.8 | −1564.8 | 7207.5 | 40493.6 |
| 20 | 41.6 | 24 | 37.8 | −162 | 25 | 61.7 | 72.7 | 146 | −2126.3 | 9043.7 | −24829.6 | 367998.5 |
| 20 | −24.6 | 4.3 | 20 | 48.9 | −58.2 | 37.8 | −63 | −38.1 | −1112.5 | −1308.3 | −5516.4 | 88586.2 |
| 20 | −24.6 | 4.3 | 37.8 | −63 | −38.1 | 37.8 | −162 | 25 | −1123.2 | −1762.2 | −6620.6 | 112360.0 |
| 20 | 48.9 | −58.2 | 37.8 | 92.4 | −8.8 | 37.8 | 127 | −95.1 | 1536.1 | 617.7 | −5468.2 | 70195.2 |
| 20 | 48.9 | −58.2 | 37.8 | 127 | −95.1 | 37.8 | 60.8 | −105 | 181.6 | −1180.1 | −3244.1 | −12680.2 |
| 20 | 48.9 | −58.2 | 37.8 | 60.8 | −105 | 37.8 | −63 | −38.1 | −1196.2 | −2203.6 | −5031.3 | 30866.4 |
| 37.8 | 92.4 | −8.8 | 37.8 | 127 | −95.1 | 61.7 | 72.7 | 146 | −2062.6 | −829.3 | 3664.5 | 44764.9 |
| 37.8 | 127 | −95.1 | 37.8 | 60.8 | −105 | 61.7 | 102 | −63 | −243.8 | 1584.6 | −2385.3 | 271840.3 |
| 37.8 | 127 | −95.1 | 61.7 | 102 | −63 | 61.7 | 72.7 | 146 | 4990.3 | 697.9 | 4324.4 | −731365.1 |
| 37.8 | 60.8 | −105 | 37.8 | −63 | −38.1 | 61.7 | −30.2 | −66 | 1606.1 | 2958.8 | 1249.9 | 166669.4 |
| 37.8 | 60.8 | −105 | 61.7 | 102 | −63 | 61.7 | −30.2 | −66 | 71.7 | −3157.2 | 5464.5 | −543370.7 |
| 37.8 | −63 | −38.1 | 37.8 | −162 | 25 | 61.7 | −161 | 33.4 | 1508.1 | 2366.1 | −888.4 | 218739.2 |
| 37.8 | −63 | −38.1 | 61.7 | −161 | 33.4 | 61.7 | −30.2 | −66 | 2375.7 | 3128.5 | 391.8 | 254053.1 |
| 37.8 | −162 | 25 | 61.7 | −161 | 33.4 | 69.5 | −132 | 89.1 | −1265.7 | 698.0 | −197.7 | −215023.8 |
| 37.8 | −162 | 25 | 69.5 | −132 | 89.1 | 61.7 | 72.7 | 146 | −2297.4 | 6713.4 | −11372.0 | −110150.0 |
| 61.7 | −161 | 33.4 | 69.5 | −132 | 89.1 | 91.7 | −83.2 | 85.3 | 1266.2 | −277.4 | −2808.0 | 386498.5 |
| 61.7 | −161 | 33.4 | 91.7 | −83.2 | 85.3 | 87 | −67.3 | −13.3 | 2714.1 | 843.1 | −8506.2 | 933905.6 |
| 61.7 | −161 | 33.4 | 87 | −67.3 | −13.3 | 61.7 | −30.2 | −66 | 2514.8 | 3311.8 | −3210.7 | 492624.0 |
| 69.5 | −132 | 89.1 | 91.7 | −83.2 | 85.3 | 91.7 | −1.2 | 145 | −1332.0 | 1820.4 | 3215.6 | −560973.0 |
| 69.5 | −132 | 89.1 | 91.7 | −1.2 | 145 | 61.7 | 72.7 | 146 | −1697.1 | 5552.6 | −4088.0 | −433958.6 |
| 91.7 | −83.2 | 85.3 | 91.7 | −1.2 | 145 | 98 | −33.9 | 95.7 | 378.0 | −516.6 | −2105.2 | 268562.4 |
| 91.7 | −83.2 | 85.3 | 98 | −33.9 | 95.7 | 87 | −67.3 | −13.3 | 572.3 | 331.9 | −5026.3 | 480221.4 |
| 91.7 | −1.2 | 145 | 98 | −33.9 | 95.7 | 98 | 8.3 | 3.3 | 582.1 | 265.9 | 5114.6 | −506939.7 |
| 91.7 | −1.2 | 145 | 61.7 | 72.7 | 146 | 76.1 | 67.7 | 4.6 | −4228.8 | −914.2 | −10432.2 | 1084383.8 |
| 91.7 | −1.2 | 145 | 76.1 | 67.7 | 4.6 | 98 | 8.3 | 3.3 | −3101.6 | −582.3 | −8447.2 | 855485.6 |
| 98 | −33.9 | 95.7 | 87 | −67.3 | −13.3 | 98 | 8.3 | 3.3 | −1016.4 | −464.2 | 7686.0 | −743256.1 |
| 87 | −67.3 | −13.3 | 61.7 | 102 | −63 | 98 | 8.3 | 3.3 | −126.7 | −3773.9 | 6566.0 | −629966.3 |
| 87 | −67.3 | −13.3 | 61.7 | 102 | −63 | 61.7 | −30.2 | −66 | −75.9 | 3342.1 | −7073.0 | 654690.6 |
| 61.7 | 72.7 | 146 | 61.7 | 102 | −63 | 76.1 | 67.7 | 4.6 | −3006.7 | −420.5 | −5167.0 | 598700.9 |
| 61.7 | 102 | −63 | 76.1 | 67.7 | 4.6 | 98 | 8.3 | 3.3 | 1499.2 | −106.4 | 4059.9 | −409962.2 |

Figure 6:
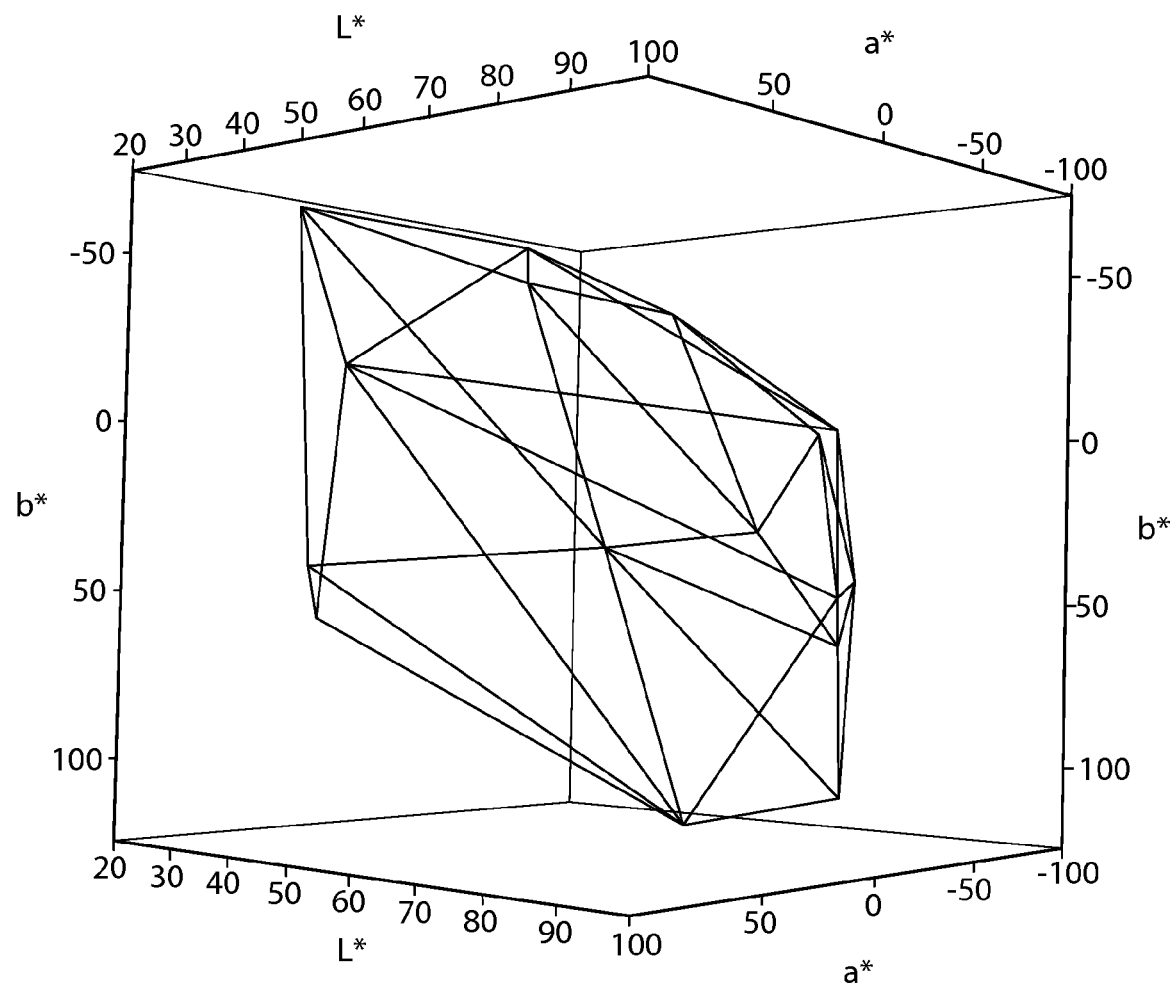
FIG. 6 is a graphical representation of exemplary extrapolated Prodoehl 3-D color gamut in CIELab (L*a*b*) coordinates.
Figure 7:
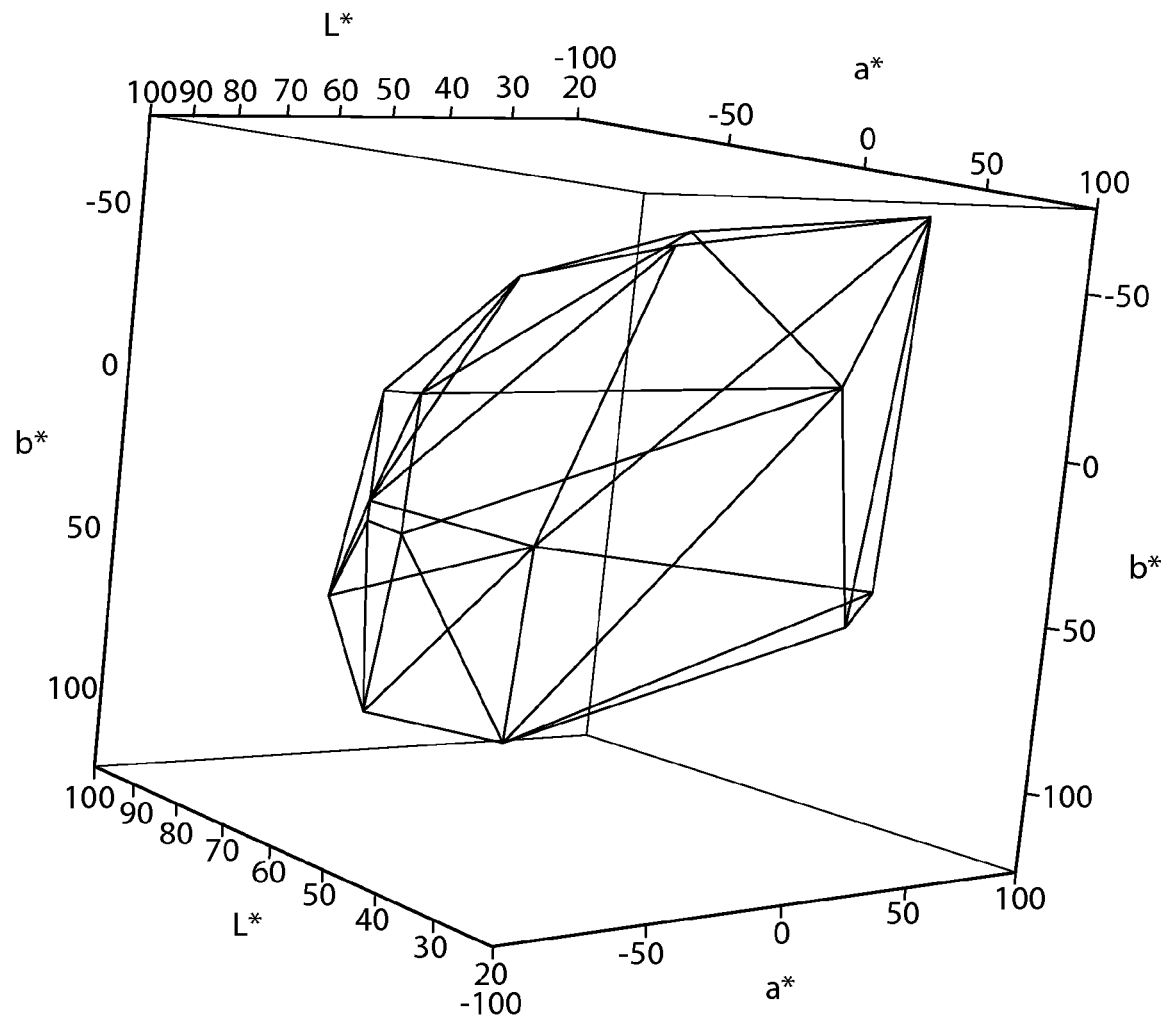
FIG. 7 is an alternative graphical representation of exemplary extrapolated Prodoehl 3-D color gamut in CIELab (L*a*b*) coordinates.

Prodoehl 3-D Color Gamut (FIGS. 6 and 7)

| Vertexes Defining Each Face ||||||||| E a* + F b* + G L* + H = 0 ||||
|---|---|---|---|---|---|---|---|---|---|---|---|---|
| Vertex 1 ||| Vertex 2 ||| Vertex 3 ||| Face Plane Equation Coefficients ||||
| z1 | x1 | y1 | z2 | x2 | y2 | z3 | x3 | y3 ||||
| L* | a* | b* | L* | a* | b* | L* | a* | b* | E | F | G | H |
| 30 | 56.6 | −67.4 | 30 | 50.6 | 42.4 | 40 | −58.9 | 34 | 1098.0 | 60.0 | 12073.5 | −420307.8 |
| 30 | 56.6 | −67.4 | 30 | 50.6 | 42.4 | 40 | 68.9 | 57.9 | 1098.0 | 60.0 | −2102.3 | 4967.4 |
| 30 | 56.6 | −67.4 | 40 | −58.9 | 34 | 40 | −18.5 | −50.7 | 847.0 | 404.0 | 5686.5 | −191299.3 |
| 30 | 56.6 | −67.4 | 40 | 68.9 | 57.9 | 50 | 82.7 | −14.6 | 1978.0 | 15.0 | −2620.9 | −32317.1 |
| 30 | 56.6 | −67.4 | 40 | −18.5 | −50.7 | 50 | 9.9 | −56.1 | 221.0 | 1035.0 | −68.7 | 59312.6 |
| 30 | 56.6 | −67.4 | 50 | 82.7 | −14.6 | 50 | 9.9 | −56.1 | 830.0 | −1456.0 | 2760.7 | −227933.1 |
| 30 | 50.6 | 42.4 | 40 | −58.9 | 34 | 80 | 20 | 113 | −1129.0 | 5169.0 | −8020.6 | 78579.5 |
| 30 | 50.6 | 42.4 | 40 | 68.9 | 57.9 | 80 | 20 | 113 | 66.0 | −1221.0 | 1771.8 | −4722.3 |
| 40 | −58.9 | 34 | 80 | 20 | 113 | 90 | −18.8 | 106 | 1069.0 | −2341.0 | 2532.4 | 41260.9 |
| 40 | −58.9 | 34 | 40 | −18.5 | −50.7 | 60 | −78 | 28.4 | −1694.0 | −808.0 | −1844.0 | 1455.8 |
| 40 | −58.9 | 34 | 60 | −78 | 28.4 | 80 | −54 | 64.3 | −830.0 | 862.0 | −551.3 | −56143.4 |
| 40 | −58.9 | 34 | 90 | −18.8 | 106 | 80 | −54 | 64.3 | 1381.0 | −1359.0 | 860.3 | 93136.1 |
| 40 | 68.9 | 57.9 | 80 | 20 | 113 | 50 | 82.7 | −14.6 | 3454.0 | 1041.0 | 2780.7 | −409483.7 |
| 80 | 20 | 113 | 50 | 82.7 | −14.6 | 93.1 | −5.6 | 48.8 | −3610.5 | −53.4 | −7318.4 | 663727.8 |
| 80 | 20 | 113 | 93.1 | −5.6 | 48.8 | 90 | −18.8 | 106 | −554.6 | −252.3 | −2326.0 | 225752.3 |
| 40 | −18.5 | −50.7 | 60 | −78 | 28.4 | 60 | −32.1 | −38.3 | 1334.0 | 918.0 | 338.0 | 57703.2 |
| 40 | −18.5 | −50.7 | 50 | 9.9 | −56.1 | 60 | −32.1 | −38.3 | −232.0 | −704.0 | 278.7 | −51133.6 |
| 60 | −78 | 28.4 | 60 | −32.1 | −38.3 | 80 | −41 | 0 | −1334.0 | −918.0 | 1164.3 | −147841.2 |
| 60 | −78 | 28.4 | 80 | −41 | 0 | 80 | −54 | 64.3 | −1286.0 | −260.0 | 2009.9 | −213518.0 |
| 50 | 82.7 | −14.6 | 94.3 | −0.3 | 2 | 50 | 9.9 | −56.1 | 1838.5 | −3225.0 | 4653.0 | −431774.4 |
| 50 | 82.7 | −14.6 | 94.3 | −0.3 | 2 | 93.1 | −5.6 | 48.8 | −2093.2 | −334.4 | −3796.4 | 358043.2 |
| 94.3 | −0.3 | 2 | 50 | 9.9 | −56.1 | 60 | −32.1 | −38.3 | 207.5 | 1758.6 | −2258.6 | 209534.8 |
| 94.3 | −0.3 | 2 | 60 | −32.1 | −38.3 | 80 | −41 | 0 | 507.7 | 941.3 | −1576.6 | 146944.1 |
| 94.3 | −0.3 | 2 | 80 | −41 | 0 | 90 | −25 | 43.3 | 599.2 | 178.2 | −1730.3 | 162991.6 |
| 94.3 | −0.3 | 2 | 90 | −25 | 43.3 | 93.1 | −5.6 | 48.8 | 151.7 | −6.9 | −937.1 | 88424.9 |
| 80 | −41 | 0 | 90 | −25 | 43.3 | 80 | −54 | 64.3 | −643.0 | −130.0 | 1591.7 | −153699.0 |
| 90 | −25 | 43.3 | 93.1 | −5.6 | 48.8 | 90 | −18.8 | 106 | −195.6 | 19.2 | 1190.0 | −112826.1 |
| 90 | −25 | 43.3 | 90 | −18.8 | 106 | 80 | −54 | 64.3 | −631.0 | 62.0 | 1960.1 | −194868.6 |

The above-described 2-D color gamuts can be approximated by drawing straight lines to between the outermost points of the respective MacAdam color gamut 30, Prodoehl color gamut 20, and Kien color gamut 10 as shown in FIG. 1. As shown, the 2-D Kien color gamut 10 absorbent paper products occupies a smaller CIELab (L*a*b*) color space than the 2-D MacAdam color gamut 30 and the 2-D Prodoehl color gamut 20. In one non-limiting embodiment, the present disclosure provides for a web substrate, such as a paper towel product, comprising colors which may be described in the 2-dimensional a*b* axes of the CIELab (L*a*b*) color space extending between the area enclosed by the system of equations describing the MacAdam color gamut 30 and Kien color gamut 10 where L*=0 to 100. In another exemplary, but non-limiting, embodiment, the present disclosure provides for a web substrate, such as a paper towel product, comprising colors which may be described in the 2-dimensional a*b* axes of the CIELab (L*a*b*) color space extending between the area enclosed by the system of equations describing the Prodoehl color gamut 20 and Kien color gamut 10 where L*=0 to 100.

In yet another exemplary, but non-limiting embodiment, the present disclosure provides for a web substrate, such as a paper towel product, comprising colors which may be described in the 3-dimensional CIELab (L*a*b*) color space extending between the area enclosed by the system of 3-D equations describing the MacAdam (FIGS. 4 and 5) and Kien (Kien) color gamut (FIGS. 2 and 3) discussed supra. In still another exemplary, but non-limiting, embodiment, the present disclosure provides for a web substrate, such as a paper towel product, comprising colors which may be described in the 3-dimensional CIELab (L*a*b*) color space extending between the area enclosed by the system of 3-D equations describing the Prodoehl (FIGS. 6 and 7) and prior art (Kien) color gamut (FIGS. 2 and 3) discussed supra.

Analytical and Testing Procedures

The following test methods are representative of the techniques utilized to determine the physical characteristics of the multi-ply tissue product associated therewith.

1. Sample Conditioning and Preparation

Unless otherwise indicated, samples are conditioned according to Tappi Method #T402OM-88. Paper samples are conditioned for at least 2 hours at a relative humidity of 48 to 52% and within a temperature range of 22° to 24° C. Sample preparation and all aspects of testing using the following methods are confined to a constant temperature and humidity room.

2. Basis Weight

Basis weight is measured by preparing one or more samples of a certain area (m$^2$) and weighing the sample(s) of a fibrous structure according to the present invention weighing at least 0.1 g on a top loading balance with a minimum resolution of 0.01 g. The balance is protected from air drafts and other disturbances using a draft shield.

Weights are recorded when the readings on the balance become constant. The average weight (g) is calculated and the average area of the samples (m$^2$). The basis weight (g/m$^2$) is calculated by dividing the average weight (g) by the average area of the samples (m$^2$).

3. Wet Burst

For the purposes of determining, calculating, and reporting 'wet burst', 'total dry tensile', and 'dynamic coefficient of friction' values infra, a unit of 'user units' is hereby utilized for the products subject to the respective test method. As would be known to those of skill in the art, bath tissue and paper toweling are typically provided in a perforated roll format where the perforations are capable of separating the tissue or towel product into individual units. A 'user unit' (uu) is the typical finished product unit that a consumer would utilize in the normal course of use of that product. In this way, a single-, double-, or even triple-ply finished product that a consumer would normally use would have a value of one user unit (uu). For example, a common, perforated bath tissue or paper towel having a single-ply construction would have a value of 1 user unit (uu) between adjacent perforations. Similarly, a single-ply bath tissue disposed between three adjacent perforations would have a value of 2 user units (2 uu). Likewise, any two-ply finished product that a consumer would normally use and is disposed between adjacent perforations would have a value of one user unit (1 uu). Similarly, any three-ply finished consumer product would normally use and is disposed between adjacent perforations would have a value of one user unit (1 uu). For purposes of facial tissues that are not normally provided in a roll format, but as a stacked plurality of discreet tissues, a facial tissue having one ply would have a value of 1 user unit (uu). An individual two-ply facial tissue product would have a value of one user unit (1 uu), etc.

Wet burst strength is measured using a Thwing-Albert Intelect II STD Burst Tester. 8 uu of tissue are stacked in four groups of 2 uu. Using scissors, cut the samples so that they are approximately 208 mm in the machine direction and approximately 114 mm in the cross-machine direction, each 2 uu thick.

Take one sample strip, holding the sample by the narrow cross direction edges, dipping the center of the sample into a flat-bottomed pan filled dimensioned proportionately larger than the sample with about 25 ml of distilled water. Leave the sample in the water four (4.0+/−0.5) seconds. Remove and drain for three (3.0+/−0.5) seconds holding the sample so the water runs off in the cross direction. Proceed with the test immediately after the drain step. Place the wet sample on the lower ring of the sample holding device with the outer surface of the product facing up, so that the wet part of the sample completely covers the open surface of the sample holding ring. If wrinkles are present, discard the sample and repeat with a new sample. After the sample is properly in place on the lower ring, turn the switch that lowers the upper ring. The sample to be tested is now securely gripped in the sample holding unit. Start the burst test immediately at this point by pressing the start button. The plunger will begin to rise. Report the maximum reading in grams force. The plunger will automatically reverse and return to its original starting position. Repeat this procedure on three more samples for a total of four tests, i.e., 4 replicates. Average the four replicates and divide this average by two to report wet burst per uu, to the nearest gram.

4. Tensile Strength

The tensile strength is determined on one inch wide strips of sample using a Thwing Albert Vontage-10 Tensile Tester (Thwing-Albert Instrument Co., 10960 Dutton Rd., Philadelphia, Pa., 19154) or equivalent. This method is intended for use on finished paper products, reel samples, and unconverted stocks.

a. Sample Conditioning and Preparation

Prior to tensile testing, the paper samples to be tested should be conditioned according to Tappi Method #T402OM-88. The paper samples should be conditioned for at least 2 hours at a relative humidity of 48 to 52% and within a temperature range of 22° to 24° C. Sample preparation and all aspects of the tensile testing should also take place within the confines of the constant temperature and humidity room.

For finished products, discard any damaged product. Take 8 uu of tissue and stack them in four stacks of 2 uu. Use stacks 1 and 3 for machine direction tensile measurements and stacks 2 and 4 for cross direction tensile measurements. Cut two 1-inch wide strips in the machine direction from stacks 1 and 3. Cut two 1-inch wide strips in the cross direction from stacks 2 and 4. There are now four 1" wide strips for machine direction tensile testing and four 1-inch wide strips for cross direction tensile testing. For these finished product samples, all eight 1" wide strips are 2 uu thick.

For unconverted stock and/or reel samples, cut a 15-inch by 15-inch sample which is twice the number of plies in a user unit thick from a region of interest of the sample using a paper cutter (JDC-1-10 or JDC-1-12 with safety shield from Thwing-Albert Instrument Co., 10960 Dutton Road, Philadelphia, Pa. 19154). Make sure one 15-inch cut runs parallel to the machine direction while the other runs parallel to the cross direction. Make sure the sample is conditioned for at least 2 hours at a relative humidity of 48 to 52% and within a temperature range of 22° C. to 24° C. Sample preparation and all aspects of the tensile testing should also take place within the confines of the constant temperature and humidity room.

From this preconditioned 15-inch by 15-inch sample which is twice the number of plies in a user unit thick, cut four strips 1-inch by 7-inch with the long 7-inch dimension running parallel to the machine direction. Note these samples as machine direction reel or unconverted stock samples. Cut an additional four strips 1-inch by 7-inch with the long 7-inch dimension running parallel to the cross direction. Note these samples as cross direction reel or unconverted stock samples. Make sure all previous cuts are made using a paper cutter (JDC-1-10 or JDC-1-12 with safety shield from Thwing-Albert Instrument Co., 10960 Dutton Road, Philadelphia, Pa., 19154). There are now a total of eight samples: four 1-inch by 7-inch strips which are twice the number of plies in a uu thick with the 7-inch dimension running parallel to the machine direction and four 1-inch by 7-inch strips which are twice the number of plies in a uu thick with the 7-inch dimension running parallel to the cross direction.

b. Operation of Tensile Tester

For the actual measurement of the tensile strength, use a Thwing Albert Vontage-10 Tensile Tester (Thwing-Albert Instrument Co., 10960 Dutton Rd., Philadelphia, Pa., 19154) or equivalent. Insert the flat face clamps into the unit and calibrate the tester according to the instructions given in the operation manual of the Thwing Albert Vontage-10. Set the instrument crosshead speed to 2.00 in/min and the 1st and 2nd gauge lengths to 4.00 inches. The break sensitivity should be set to 20.0 grams and the sample width should be set to 1.00 inches and the sample thickness at 0.025 inches.

A load cell is selected such that the predicted tensile result for the sample to be tested lies between 25% and 75% of the range in use. For example, a 5000 gram load cell may be used for samples with a predicted tensile range of 1250 grams (25% of 5000 grams) and 3750 grams (75% of 5000 grams). It is preferred to use a 500 gram load cell.

Take one of the tensile strips and place one end of it in one clamp of the tensile tester. Place the other end of the paper strip in the other clamp. Make sure the long dimension of the strip is running parallel to the sides of the tensile tester. Also make sure the strips are not overhanging to the either side of the two clamps. In addition, the pressure of each of the clamps must be in full contact with the paper sample.

After inserting the paper test strip into the two clamps, the instrument tension can be monitored. If it shows a value of 5 grams or more, the sample is too taut. Conversely, if a period of 2-3 seconds passes after starting the test before any value is recorded, the tensile strip is too slack.

Start the tensile tester as described in the tensile tester instrument manual. The test is complete after the crosshead automatically returns to its initial starting position. Read and record the maximum tensile load in units of grams from the instrument scale or the digital panel meter to the nearest unit of 1 gram force.

If the reset condition is not performed automatically by the instrument, perform the necessary adjustment to set the instrument clamps to their initial starting positions. Insert the next paper strip into the two clamps as described above and obtain a tensile reading in units of grams. Obtain tensile readings from all the paper test strips. It should be noted that readings should be rejected if the strip slips or breaks in or at the edge of the clamps while performing the test.

c. Calculations

For the four machine direction 1-inch wide finished product strips, average the four individual recorded tensile readings. Divide this average by the number of user unit tested (e.g., 2) to get the MD dry tensile per user unit of the sample. Repeat this calculation for the cross direction finished product strips. To calculate total dry tensile of the sample, sum the MD dry tensile and CD dry tensile. All results are in units of grams force/inch.

To calculate the Wet Burst/Total Dry Tensile ratio divide the average wet burst by the total dry tensile. The results are in units of inches.

5. Tensile Modulus

Tensile Modulus of tissue samples is obtained at the same time as the tensile strength of the sample is determined. In this method a single ply 10.16 cm wide sample is placed in a tensile tester (e.g., Thwing Albert QCII interfaced to an LMS data system) with a gauge length of 5.08 cm. The sample is elongated at a rate of 2.54 cm/minute. The sample elongation is recorded when the load reaches 10 g/cm (F10), 15 g/cm (F15), and 20 g/cm ($F_{20}$). A tangent slope is then calculated with the mid-point being the elongation at 15 g/cm (F15).

The Tangent slope is calculated in the following manner:

$$\text{Tangent Slope } (TenMod15) = \frac{(\text{delta force})}{(\text{delta elongation})}$$
$$= \frac{(F20 - F10)}{(\% \text{ elongation } @F20 - \% \text{ elongation } @F10)}$$

Another exemplary method for obtaining the tangent slope at 15 g/cm is to use a Thwing-Albert STD tensile tester and set the load trap to 152.4 grams in the tangent slope calculation program. This is equivalent to 15 g/cm when using the 10.16 cm width sample.

Total Tensile Modulus is obtained by measuring the Tensile Modulus in the machine direction at 15 g/cm and cross machine direction at 15 g/cm and then calculating the geometric mean. Mathematically, this is the square root of the product of the machine direction Tensile Modulus (TenMod15MD) and the cross direction Tensile Modulus (TenMod15CD).

TotalTensileModulus=(TenMod15MD× TenMod15CD)$^{1/2}$

High values for Total Tensile Modulus indicate that the sample is stiff and rigid.

6. Bulk Density

Bulk density or 'density' is the mathematical relationship of the basis weight of a sample divided by its thickness (i.e., caliper) incorporating appropriate unit conversions as required. Bulk density as used herein has units of $g/cm^3$.

7. Color Test Method

CIELab (L*a*b*) values of a finally printed product produced according to the present disclosure discussed herein can be measured with a colorimeter, spectrophotometer, or spectrodensitometer according to ISO 13655. A suitable spectrodensitometer for use with this invention is the X-Rite530 commercially available from X-Rite, Inc. of Grand Rapids, Mich.

Select the D50 illuminant and 2 degree observer as described. Use 45/0° measurement geometry. The spectrodensitometer should have a 10 nm measurement interval. The spectrodensitometer should have a measurement aperture of less than 2 mm. Before taking color measurements, calibrate the spectrodensitometer according to manufacturer instructions. Visible surfaces are tested in a dry state and at an ambient relative humidity of approximately 50%±2% and a temperature of 23° C.±1° C. Place the sample to be measured on a white backing that meets ISO 13655 section A3 specifications. Exemplary white backings are described on the web site: http://www.fogra.de/en/fogra-standardization/fogra-characterizationdata/information-about-measurement-backings/. Select a sample location on the visible surface of the printed product containing the color to be analyzed. The L*, a*, and b* values are read and recorded.

In a preferred embodiment, the product of the present disclosure has a basis weight of greater than 18 $g/m^2$, more preferably ranging from about 18.1 $g/m^2$ to about 50 $g/m^2$, most preferably from about 19 $g/m^2$ to about 25 $g/m^2$ as determined by the basis weight test method described infra. In a preferred embodiment, the product of the present disclosure has a wet burst value of greater than about 900 g, more preferably ranging from about 90 g and 500 g, most preferably from about 100 g and 350 g, and even more preferably from about 125 g to about 200 g as determined by the wet burst test method described infra. In a preferred embodiment, the product of the present disclosure has a total dry tensile strength value of greater than about 500 g/in, more preferably ranging from about 500 g/in and 1500 g/in, most preferably from about 700 g/in and about 1000 g/in as determined by the total tensile test method described infra. In a preferred embodiment, the product of the present disclosure has a bulk density value ranging from about 0 $g/cm^3$ to about 0.1 $g/cm^3$, more preferably about 0.04 $g/cm^3$ and about 0.08 $g/cm^3$ as determined by the bulk density test method as described infra.

The dimensions and values disclosed herein are not to be understood as being strictly limited to the exact dimension and values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A web substrate having indicia comprising at least 2 colors comprising X fluids disposed thereon, said indicia being disposed upon said web substrate by a contact printing system comprising a gravure cylinder having an outer surface for contacting said web substrate and being adapted to print said X fluids each disposed at a position internal to said gravure cylinder and directable to said outer surface and into contacting engagement with said web substrate utilizing X-Y printing components where X and Y are whole numbers, 0<Y<X, and X>1, each of said at least 2 colors being defined by L*a*b* color values defined by CIELab coordinate values disposed inside a boundary described by the following system of equations:

$$\{a^*=-54.1 \text{ to } 72.7; b^*=131.5 \text{ to } 145.8\} \rightarrow b^*=0.113 a^*+137.6$$

$$\{a^*=-131.6 \text{ to } -54.1; b^*=89.1 \text{ to } 131.5\} \rightarrow b^*=0.547 a^*+161.1$$

$$\{a^*=-165.6 \text{ to } -131.6; b^*=28.0 \text{ to } 89.1\} \rightarrow b^*=1.797 a^*+325.6$$

$$\{a^*=3.6 \text{ to } -165.6; b^*=-82.6 \text{ to } 28.0\} \rightarrow b^*=-0.654 a^*-80.3$$

$$\{a^*=127.1 \text{ to } 3.6; b^*=-95.1 \text{ to } -82.6\} \rightarrow b^*=-0.101 a^*-82.3$$

$$\{a^*=72.7 \text{ to } 127.1; b^*=145.8 \text{ to } -95.1\} b^*=-4.428 a^*+467.7$$

where L* ranges from 0 to 100; and, wherein said indicia disposed upon said web substrate has a dot gain of less than 20% and a 1:1 relationship between input halftone density and output halftone density.

2. The web substrate of claim 1, wherein each of said at least 2 colors is defined by CIELab coordinate values disposed inside a boundary described by the following system of equations:

$$\{a^*=20.0 \text{ to } 63.6; b^*=113.3 \text{ to } 75.8\} \rightarrow b^*=-0.860 a^*+130.50$$

$$\{a^*=-47.5 \text{ to } 20.0; b^*=82.3 \text{ to } 113.3\} \rightarrow b^*=0.459 a^*+104.11$$

$$\{a^*=-78.0 \text{ to } -47.5; b^*=28.4 \text{ to } 82.3\} \rightarrow b^*=1.767 a^*+166.24$$

$$\{a^*=-18.8 \text{ to } -78.0; b^*=-51.7 \text{ to } 28.4\} \rightarrow b^*=-1.353 a^*-77.14$$

$$\{a^*=56.6 \text{ to } -18.8; b^*=-67.4 \text{ to } -51.7\} \rightarrow b^*=-0.208 a^*-55.61$$

$$\{a^*=81.8 \text{ to } 56.6; b^*=-29.8 \text{ to } -67.4\} \rightarrow b^*=1.492 a^*-151.85$$

$$\{a^*=63.6 \text{ to } 81.8; b^*=75.8 \text{ to } -29.8\} \rightarrow b^*=-5.802 a^*+444.82$$

where L* ranges from 0 to 100.

3. The web substrate of claim 1 further comprising a basis weight of greater than 18 g/m².

4. The web substrate of claim 3 further comprising a basis weight ranging from about 18.1 g/m² to about 50 g/m².

5. The web substrate of claim 1 further comprising a wet burst value of greater than about 90 g.

6. The web substrate of claim 5 further comprising a wet burst value ranging from about 90 g to about 500 g.

7. The web substrate of claim 6 further comprising a wet burst value ranging from about 125 g to about 200 g.

8. The web substrate of claim 1 further comprising a total dry tensile strength value of greater than about 500 g/in.

9. The web substrate of claim 8 further comprising a total dry tensile strength value ranging from 500 g/in to 1500 g/in.

10. The web substrate of claim 1 further comprising a bulk density value ranging from about 0 g/cm³ to about 0.1 g/cm³.

11. The web substrate of claim 10 further comprising a bulk density value ranging from about 0.04 g/cm³ to about 0.08 g/cm³.

12. The web substrate of claim 1 wherein said L*a*b* color values are determined by a color test method as described herein.

13. The web substrate of claim 12 wherein said color test method incorporates ISO 13655.

14. The web substrate of claim 1 wherein said indicia has a dot gain of less than 5%.

15. The web substrate of claim 1 wherein said indicia has a smooth tone gradient over an entire tonal range of said indicia.

16. The web substrate of claim 1 further comprising an MD and/or CD modulus of less than about 20,000 g/cm at a load of about 15 g.

17. The web substrate of claim 1 further comprising a halftone value of greater than 20 dpi.

18. The web substrate of claim 17 further comprising a halftone value of greater than 85 dpi.

* * * * *